United States Patent
Alani et al.

(10) Patent No.: US 10,174,385 B2
(45) Date of Patent: Jan. 8, 2019

(54) ASSAYS AND METHODS RELATING TO THE TREATMENT OF MELANOMA

(71) Applicant: TRUSTEES OF BOSTON UNIVERSITY, Boston, MA (US)

(72) Inventors: Rhoda M. Alani, Newton, MA (US); Byungwoo Ryu, Wayland, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 153 days.

(21) Appl. No.: 15/105,192

(22) PCT Filed: Dec. 19, 2014

(86) PCT No.: PCT/US2014/071456
§ 371 (c)(1),
(2) Date: Jun. 16, 2016

(87) PCT Pub. No.: WO2015/095686
PCT Pub. Date: Jun. 25, 2015

(65) Prior Publication Data
US 2016/0312300 A1    Oct. 27, 2016

Related U.S. Application Data

(60) Provisional application No. 61/919,064, filed on Dec. 20, 2013.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/112* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 2009/0220472 A1 | 9/2009 | Winqvist et al. | |
| 2010/0172921 A1* | 7/2010 | Wu | C07K 16/2863 424/174.1 |
| 2011/0091377 A1 | 4/2011 | Alani et al. | |
| 2011/0091384 A1* | 4/2011 | Alani | G01N 33/5743 424/9.1 |

FOREIGN PATENT DOCUMENTS

| WO | 2008/141275 A1 | 11/2008 | |
|---|---|---|---|
| WO | WO2008141275 | * 11/2008 | ............... C12Q 1/68 |

OTHER PUBLICATIONS

Brownbridge et al. Evaluation of the use of tyrosinase-specific and melanA/MART-1-specific reverse transcriptase-coupled-polymerase chain reaction to detect melanoma cells in peripheral blood samples from 299 patients with malignant melanoma. Br J Dermatol. Feb. 2001; 144(2):279-87. (Year: 2007).*
Rossi M, Tuck J, Kim OJ, Panova I, Symanowski JT, Mahalingam M, Riker AI, Alani RM, Ryu B. Neuropilin-2 gene expression correlates with malignant progression in cutaneous melanoma. Br J Dermatol. Aug. 2014; 171(2):403-8. Epub Jun. 11, 2014. (Year: 2014).*
Sørensen BS, Schmidt H, von der Maase H, Straten PT, Nexo E. Quantification of melanoma cell-specific MART-1 mRNA in peripheral blood by a calibrated competitive reverse transcription-PCR. Clin Chem. Dec. 2000; 46(12):1923-8. (Year: 2000).*
Tanaka R, Koyanagi K, Narita N, Kuo C, Hoon DS. Prognostic molecular biomarkers for cutaneous malignant melanoma. J Surg Oncol. Sep. 2011; 104(4):438-46. Epub May 9, 2011. Review. (Year: 2011).*
Toussaint JF, Sailleau C, Breard E, Zientara S, De Clercq K. Bluetongue virus detection by two real-time RT-qPCRs targeting two different genomic segments. J Virol Methods. Mar. 2007; 140(1-2):115-23. Epub Dec. 28, 2006. (Year: 2007).*
Wang C, Gao D, Vaglenov A, Kaltenboeck B. One-step real-time duplex reverse transcription PCRs simultaneously quantify analyte and housekeeping gene mRNAs. Biotechniques. Mar. 2004; 36(3):508-16, 518-9. (Year: 2004).*
Wang J, Jia R, Yao Y, Cun B, Huang X, Gu P, Ge S, Fan X. Differential expression of Mart-1 in human uveal melanoma cells. Mol Med Rep. Sep.-Oct. 2011; 4(5):799-803. Epub Jun. 7, 2011. (Year: 2011).*
Dawson ED, Taylor AW, Smagala JA, Rowlen KL. Molecular detection of *Streptococcus pyogenes* and *Streptococcus dysgalactiae* subsp. *equisimilis*. Mol Biotechnol. May 2009; 42(1):117-27. Epub Jan. 21, 2009. (Year: 2009).*
Murer K, Urosevic M, Willers J, Selvam P, Laine E, Burg G, Dummer R. Expression of Melan-A/MART-1 in primary melanoma cell cultures has prognostic implication in metastatic melanoma patients. Melanoma Res. Aug. 2004; 14(4):257-62. (Year: 2004).*
Riber-Hansen R, Abrahamsen HN, Sorensen BS, Hamilton-Dutoit SJ, Steiniche T. Quantitative real-time RT-PCR in sentinel lymph nodes from melanoma patients. Detection of melanocytic mRNA predicts disease-free survival. APMIS. Mar. 2008; 116(3):199-205. (Year: 2008).*
Nazarian et al., "Melanoma biomarker expression in melanocytic tumor progression: a tissue microarray study", Cutan Pathol. 37(Suppl. 1):41-47 (2010).
Wititsuwannakul et al., "Neuropilin-2 as a useful marker in the differentiation between Spitzoid malignant melanoma and Spitz nevus", J Am Acad Dermatol. 68(1):129-137 (2013).

(Continued)

*Primary Examiner* — Aaron A Priest
*Assistant Examiner* — Olayinka A Oyeyemi
(74) *Attorney, Agent, or Firm* — Nixon Peabody LLP; Ronald I. Eisenstein; Nicole D. Kling

(57) ABSTRACT

The technology described herein relates to assays and methods for the diagnosis, prognosis, and/or treatment of melanoma, e.g. relating to measuring the level of neurophilin-2 (NRP-2) mRNA expressed in melanoma cells. In some embodiments, the level of NRP-2 can be normalized to the level of Melan-A (MART) mRNA.

17 Claims, 8 Drawing Sheets

Specification includes a Sequence Listing.

(56) References Cited

OTHER PUBLICATIONS

Cronin et al., "Measurement of Gene Expression in Archival Paraffin-Embedded Tissues: Development and Jerformance of a 92-Gene Reverse Transcriptase-Polymerase Chain Reaction Assay", American Journal of Pathology 164(1):35-42 (2004).

Fringuelli et al., "Detection of Neoparamoeba perurans by duplex quantitative Taqman real-time PCR in formalin-fixed, paraffin-embedded Atlantic salmonid gill tissues", Journal of Fish Diseases 35(10):711-724 (2012).

Lebbe et al., "A Reliable Method for the Selection of Exploitable Melanoma Archival Paraffin Embedded Tissues for Transcript Biomarker Profiling", PLoS One 7(1):e29143 (2012).

Linton et al., "Acquisition of biologically relevant gene expression data by Affymetrix microarray analysis of archival formalin-fixed paraffin-embedded tumours", British Journal of Cancer 98(8):1403-1414 (2008).

Nielsen et al., "Automated Quantification of MART1-Verified Ki67 Indices by Digital Image Analysis in Melanocytic Lesions", Arch Pathol Lab Met 136(6):627-634 (2012).

Paik et al., "A Multigene Assay to Predict Recurrence of Tamoxifen-Treated, Node-Negative Breast Cancer", N Engl J Med. 351(27):2817-2826 (2004).

Rushing et al., "Neuropilin-2: a novel biomarker for malignant melanoma?", Hum Pathol. 43(3):381-389 (2012).

Ryu et al., "Comprehensive Expression Profiling of Tumor Cell Lines Identifies Molecular Signatures of Melanoma Progression", PLoS One 2(7):e594 (2007).

\* cited by examiner

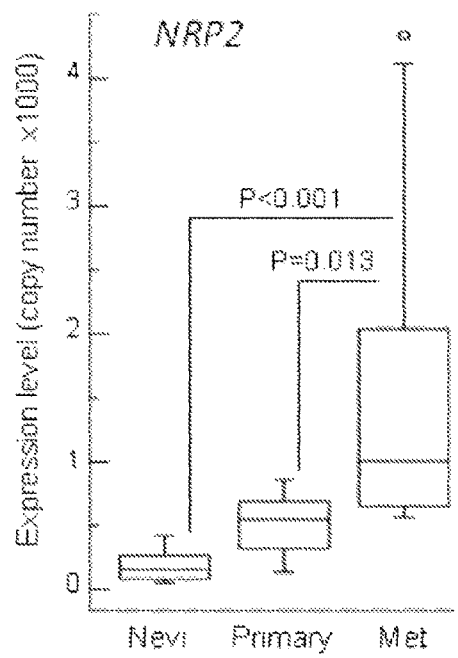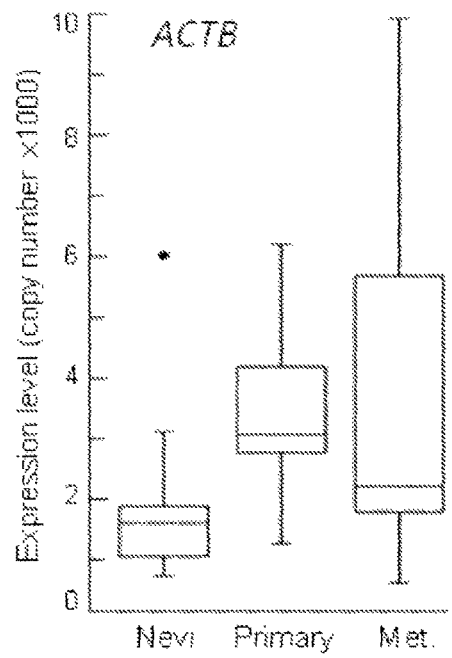
Fig. 1A   Fig. 1B
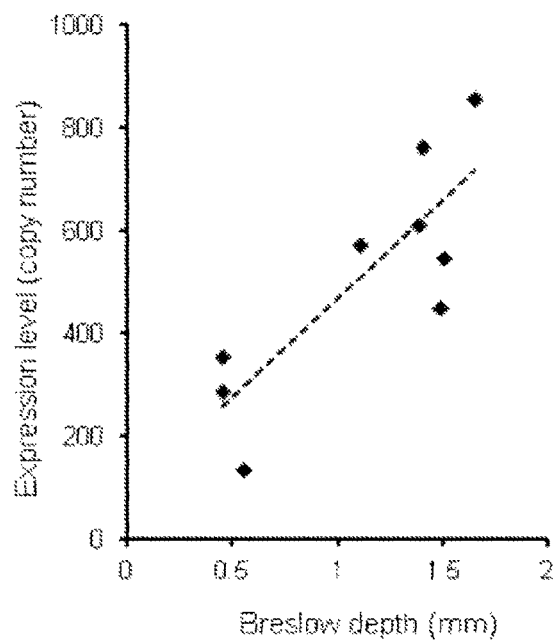
Fig. 1C

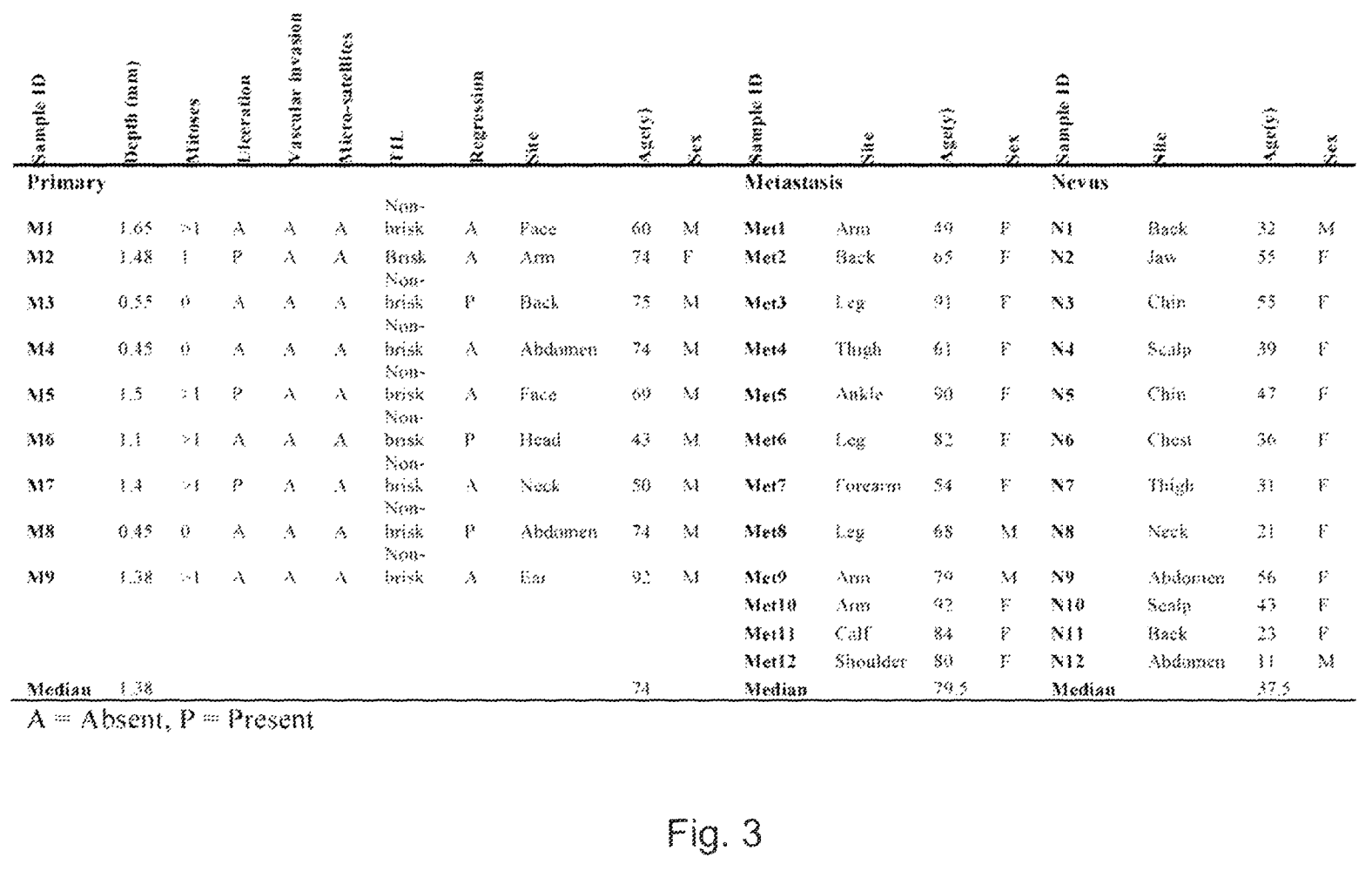

| Primary | | | | | | | | | | | Metastasis | | | | | Nevus | | | |
|---|---|---|---|---|---|---|---|---|---|---|---|---|---|---|---|---|---|---|---|
| Sample ID | Depth (mm) | Mitoses | Ulceration | Vascular invasion | Micro-satellites | TIL | Regression | Site | Age(s) | Sex | Sample ID | Site | Age(s) | Sex | Sample ID | Site | Age(s) | Sex |
| M1 | 1.65 | >1 | A | A | A | Non-brisk | A | Face | 60 | M | Met1 | Arm | 44 | F | N1 | Back | 32 | M |
| M2 | 1.48 | 1 | P | A | A | Brisk | A | Arm | 74 | F | Met2 | Back | 65 | F | N2 | Jaw | 55 | F |
| M3 | 0.55 | 0 | A | A | A | Non-brisk | P | Back | 75 | M | Met3 | Leg | 91 | F | N3 | Chin | 45 | F |
| M4 | 0.85 | 0 | A | A | A | Non-brisk | A | Abdomen | 74 | M | Met4 | Thigh | 61 | F | N4 | Scalp | 39 | F |
| M5 | 1.5 | >1 | P | A | A | Non-brisk | A | Face | 69 | M | Met5 | Ankle | 50 | F | N5 | Chin | 47 | F |
| M6 | 1.1 | >1 | A | A | A | Brisk | P | Head | 43 | M | Met6 | Leg | 82 | F | N6 | Chest | 36 | F |
| M7 | 1.4 | >1 | A | A | A | Non-brisk | A | Neck | 50 | M | Met7 | Forearm | 54 | F | N7 | Thigh | 31 | F |
| M8 | 0.45 | 0 | P | A | A | Brisk | P | Abdomen | 74 | M | Met8 | Leg | 68 | M | N8 | Neck | 21 | F |
| M9 | 1.38 | >1 | A | A | A | Non-brisk | A | Ear | 92 | M | Met9 | Arm | 70 | M | N9 | Abdomen | 56 | F |
| | | | | | | | | | | | Met10 | Arm | 92 | F | N10 | Scalp | 43 | F |
| | | | | | | | | | | | Met11 | Calf | 84 | P | N11 | Back | 22 | F |
| | | | | | | | | | | | Met12 | Shoulder | 80 | F | N12 | Abdomen | 11 | M |
| Median | 1.38 | | | | | | | | 73 | | Median | | 74.5 | | Median | | 37.5 | |

A = Absent, P = Present

Fig. 3

| Primary melanoma | | | | | | | | | | | | | |
|---|---|---|---|---|---|---|---|---|---|---|---|---|---|
| Sample ID | M1 | M2 | M3 | M4 | M5 | M6 | M7 | M8 | M9 | M10 | M11 | M12 | Median |
| Depth (mm) | 1.65 | 1.48 | 0.55 | 0.45 | 1.5 | 1.71 | 1.3 | 0.45 | 1.38 | | | | |
| Mitosis | >1 | 1 | 0 | 0 | >1 | >1 | >1 | 0 | >1 | | | | |
| Ulceration | A | P | A | A | P | A | P | A | A | | | | |
| Micro-satellites | A | A | A | A | A | A | A | A | A | | | | |
| TIL | Non-brisk | Brisk | Non-brisk | Non-brisk | Non-brisk | Non-brisk | Non-brisk | Non-brisk | Non-brisk | | | | |
| Regression | A | A | P | A | A | P | A | P | A | | | | |
| Site | Face | Arm | Back | Abdomen | Face | Head | Neck | Abdomen | Ear | | | | |
| Age (y) | 86 | 74 | 75 | 74 | 89 | 43 | 50 | 74 | 92 | | | | 74 |
| Sex | M | F | M | M | M | M | M | M | M | | | | |

| Metastatic melanoma | | | | | | | | | | | | | |
|---|---|---|---|---|---|---|---|---|---|---|---|---|---|
| Sample ID | Met1 | Met2 | Met3 | Met4 | Met5 | Met6 | Met7 | Met8 | Met9 | Met10 | Met11 | Met12 | Median |
| Site | Arm | Back | Leg | Thigh | Ankle | Leg | Forearm | Leg | Arm | Arm | Calf | Shoulder | |
| Type of lesion | Skin | Skin | Skin | Skin | Skin | Skin | Skin | Lymph node | Lymph node | Lymph node | Skin | Skin | |
| Age (y) | 49 | 85 | 91 | 61 | 90 | 82 | 54 | 68 | 79 | 92 | 83 | 80 | 79.5 |
| Sex | F | F | F | F | F | F | F | M | M | F | F | F | |

| Naevus | | | | | | | | | | | | | |
|---|---|---|---|---|---|---|---|---|---|---|---|---|---|
| Sample ID | N1 | N2 | N3 | N4 | N5 | N6 | N7 | N8 | N9 | N10 | N11 | N12 | Median |
| Site | Back | Jaw | Chin | Scalp | Chin | Chest | Thigh | Neck | Abdomen | Scalp | Back | Abdomen | |
| Subtype | IC | CC | I | I | I | I | IC | C | C | I | C | C | |
| Age (y) | 32 | 55 | 55 | 39 | 47 | 36 | 31 | 21 | 56 | 43 | 23 | 33 | 37.5 |
| Sex | M | F | F | F | F | F | F | F | F | F | F | M | |

TIL, tumour-infiltrating lymphocytes; A, absent; P, present; I, intradermal melanocytic naevus; C, compound melanocytic naevus; IC, intradermal melanocytic naevus with congenital features; CC, compound melanocytic naevus with congenital features

Fig. 7

SEQUENCE LISTING

<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gactccaagc ccacggtaga                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tggttgtctc ttcgctcttc ac                                           22

<210> SEQ ID NO 3
<211> LENGTH: 14
<212> TYPE: DNA
<213> ORGANISM: Artificial Sequence
<220> FEATURE:

```
<223> OTHER INFORMATION: Description of Artificial Sequence: Synthetic
      probe
<220> FEATURE:
<223> OTHER INFORMATION: 5' 6FAM/3' MGBNFQ

<400> SEQUENCE: 3
acgctgggac ccac                                                         14

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagctcacc atggatgatg                                                   20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atgccggagc cgttgtc                                                      17

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 6FAM/3' MGBNFQ

<400> SEQUENCE: 6
tatcgccgcg ctcg                                                         14

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggccatcca atttctcttt actt                                              24

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgtcggtca aggttcgaaa a                                                 21

<210> SEQ ID NO 9
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' 6FAM/3' MGBNFQ

<400> SEQUENCE: 9
ttggctaata acaaactagt ca                                            22

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgatgacgcc ggtgaac                                                  17

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtctttccg tgctccaaaa                                               20

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5' VIC/3' MGBNFQ

<400> SEQUENCE: 12
tcccgccgcc gtt                                                      13

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggatgcggct ggaggtgctg                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccgccctggt cctcacggat                                               20
```

```
<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agaacagtca ccaccacct                                                   19

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggccagtcaa ccctttgtct taacc                                            25

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22
<211> LENGTH: 6671
<212> TYPE: DNA
<213> ORGANISM: Homo sapiens

<400> SEQUENCE: 22
cagagatcgc gagcgaggca ccagcctgca gccggccccc agcacatcct cagccgcaca     60
gacactcggc gaggtggagg tgagggcggg cgccagcgaa ctcggagagg ggctcgctca    120
ctcccaggcg atcccagccg ccaccgccgc cgcaccagca gcagcaacag cagcagcagc    180
ttccttcctc agactcccct cgagaggctg gccaagcggg tgtagccgtt ggggaggct     240 cccgccgggg gaacccggcg aggacaagag cagggcggcc gccttccact cgggctgtcc    300
```

```
ggcggcggct gcctccgccc gtgtgtccgt caagggtgcc gcgggatgtg tgtcagttta      360
cgcctctgag atcacacagc tgcctggggg ccgtgtgatg cccaaggcaa gtcttggttt      420
taattattat tattatcatt attgttacgc ttggctttcg ggaaatactc gtgatatttg      480
taggataaag gaaatgacac tttgaggaac tggagagaac atatatgcgt tttgttttta      540
agaggaaaac cgtgttctct tcccggcttg ttccctcttt gctgatttca ggagctactc      600
tcctcctggt gaggtggaaa ttccagcaag aatagaggtg aagacaagcc accaggactc      660
aggagggaaa cgctgaccat tagaaacctc tgcataagac gttgtaagga ggaaaataaa      720
agagagaaaa acacaaagat ttaaacaaga aacctacgaa cccagctctg aaagagcca      780 ccttctccaa aatggatatg tttcctctca cctgggtttt cttagccctc tacttttcaa      840
gacaccaagt gagaggccaa ccagacccac cgtgcgaggt cgtttgaatt ccaaagatg      900 ctggctatat cacctctccc ggttaccccc aggactaccc ctcccaccag aactgcgagt      960
ggattgttta cgcccccgaa cccaaccaga agattgtcct caacttcaac cctcactttg     1020
aaatcgagaa gcacgactgc aagtatgact ttatcgagat tcgggatggg acagtgaat     1080 ccgcagacct cctgggcaaa cactgtggga acatcgcccc gcccaccatc atctcctcgg     1140
gctccatgct ctacatcaag ttcacctccg actacgcccg gcaggggca ggcttctctc     1200 tgcgctacga gatcttcaag acaggctctg aagattgctc aaaaaacttc acaagcccca     1260
acgggaccat cgaatctcct gggtttcctg agaagtatcc acacaacttg gactgcacct     1320
ttaccatcct ggccaaaccc aagatggaga tcatcctgca gttcctgatc tttgacctgg     1380
agcatgaccc tttgcaggtg ggagagggg actgcaagta cgattggctg acatctgggg     1440
atggcattcc acatgttggc cccctgattg gcaagtactg tgggaccaaa cacccctctg     1500
aacttcgttc atcgacgggg atcctctccc tgaccttca cacggacatg gcggtggcca     1560
aggatggctt ctctgcgcgt tactacctgg tccaccaaga gccactagag aactttcagt     1620
gcaatgttcc tctgggcatg gagtctggcc ggattgctaa tgaacagatc agtgcctcat     1680
ctacctactc tgatgggagg tggacccctc aacaaagccg gctccatggt gatgacaatg     1740
gctggacccc caacttggat tccaacaagg agtatctcca ggtggacctg cgcttttaa     1800 ccatgctcac ggccatcgca acacagggag cgatttccag ggaaacacag aatggctact     1860
atgtcaaatc ctacaagctg gaagtcagca ctaatggaga ggactggatg gtgtaccggc     1920
atggcaaaaa ccacaaggta tttcaagcca acaacgatgc aactgaggtg gttctgaaca     1980
agctccacgc tccactgctg acaaggtttg ttagaatccg ccctcagacc tggcactcag     2040
gtatcgccct ccggctggag ctcttcggct gccgggtcac agatgctccc tgctccaaca     2100
tgctggggat gctctcaggc ctcattgcag actcccagat ctccgcctct tccacccagg     2160
aatacctctg gagcccagt gcagcccgcc tggtcagcag ccgctcgggc tggttccctc     2220
gaatccctca ggcccagccc ggtgaggagt ggcttcaggt agatctggga acacccaaga     2280
cagtgaaagg tgtcatcatc cagggagccc gcggaggaga cagtatcact gctgtggaag     2340
ccagagcatt tgtgcgcaag ttcaaagtct cctacagcct aaacggcaag gactgggaat     2400
acattcagga cccaggacc cagcagccaa agctgttcga agggaacatg cactatgaca     2460 ccctgacat ccgaaggttt gaccccattc cggcacagta tgtgcgggta cccggaga     2520 ggtggtcgcc ggcggggatt gggatgcggc tggaggtgct gggctgtgac tggacagact     2580
ccaagcccac ggtagagacg ctgggaccca ctgtgaagag cgaagagaca accacccct     2640 accccaccga agaggaggcc acagagtgtg gggagaactg cagctttgag gatgacaaag     2700
```

```
atttgcagct cccttcggga ttcaattgca acttcgattt cctcgaggag ccctgtggtt    2760
ggatgtatga ccatgccaag tggctccgga ccacctgggc cagcagctcc agcccaaacg    2820
accggacgtt tccagatgac aggaatttct tgcggctgca gagtgacagc cagagagagg    2880
gccagtatgc ccggctcatc agccccctg tccacctgcc ccgaagcccg gtgtgcatgg     2940
agttccagta ccaggccacg ggcggccgcg gggtggcgct gcaggtggtg cgggaagcca    3000
gccaggagag caagttgctg tgggtcatcc gtgaggacca gggcggcgag tggaagcacg    3060
ggcggatcat cctgcccagc tacgacatgg agtaccagat tgtgttcgag ggagtgatag    3120
ggaaaggacg ttccggagag attgccattg atgacattcg dataagcact gatgtcccac    3180
tggagaactg catggaaccc atctcggctt ttgcaggtga aatttttaaa gtggacatcc    3240
cagaaataca tgagagagaa ggatatgaag atgaaattga tgatgaatac gaggtggact    3300
ggagcaattc ttcttctgca acctcagggt ctggcgcccc ctcgaccgac aaagaaaaga    3360
gctggctgta caccctggat ccatcctca tcaccatcat cgccatgagc tcactgggcg     3420
tcctcctggg ggccacctgt gcaggcctcc tgctctactg cacctgttcc tactcgggcc    3480
tgagctcccg aagctgcacc acactggaga actacaactt cgagctctac gatggcctta    3540
agcacaaggt caagatgaac caccaaaagt gctgctccga ggcatgacgg attgcacctg    3600
aatcctatct gacgtttcat tccagcaaga ggggctgggg aagattacat tttttttcc     3660 tttgaaaact gaatgccata atctcgatca aaccgatcca gaataccgaa ggtatggaca    3720
ggacagaaaa gcgagtcgca ggaggaaggg agatgcagcc gcacagggga tgattaccct    3780
cctaggaccg cggtggctaa gtcattgcag gaacggggct gtgttctctg ctgggacaaa    3840
acaggagctc atctctttgg ggtcacagtt ctattttgtt tgtgagtttg tattattatt    3900
attattatta ttattattat attttatttc tttggtctgt gagcaactca aagaggcaga    3960
agaggagaat gactttttcca gaatagaagt ggagcagtga tcattattct ccgctttctc    4020
tttctaatca acacttgaaa agcaaagtgt cttttcagcc tttccatctt tacaaataaa    4080
actcaaaaaa gccgtccagc ttatcccatc ctctgattgt cttctgactt aagggattta    4140
ctgtggtgta ggttctgcca gccaaccctc aaagctgcca tttccagtcc tagcatttaa    4200
gtaggatgtt gttgccttta acttttctta tccaggggaa aattgccatt ttagggtcag    4260
catgaacagc tctttcttgt atgcgattta aaacaaactg gaaaggaaac ttcacacgtc    4320
aaaatccata gaagcgcctg gacgaggctt aaagtgcttt gtgagtgaat aggagccatt    4380
cgctaattct agaccacag tgtctggtgg tgggcttcc cttgtgggc ttctggtggt       4440 ggttttgcct tttctttttcc ctcctccatg ttcttctaaa acatatacat atatacatac    4500
acacatacac atattcttca ggtctctaag ccctggaag cagcattgtg tgatattctc     4560
agaggcaggg gaaatagag ggaaaaatag agactattgg tatgttctcc ccatcagcga     4620
gttattgtaa ctggtcacca ctggacggga aggagaacag aggagaggga aagagaagcc    4680
caacctctgt gatcatatga gggccaaggc tgagcagtgt agacagagac cctttgaaat    4740
gcatttgtct ctcaaataga ctagtaaaca ccgacttctc ctttgggtta caaacaccat    4800
ttcaaccttt cgggagagtc agagctagga tgtacaagaa ctgattctaa ccagaagtcc    4860
gcaagtactg tggacaagaa tgcttaacca tgctgcttca gccttgagag acctaggttc    4920
ttacacatat gcacacacgc atacacacat gcacgcacac acacatacac acatgcacgc    4980
acgcacgcat gcacaccaat ttatgttttt attaagtgcc ttgaaaaaat gaagaaaaat    5040
```

```
                                  -continued
gtattttccc tttatgtaaa aattagtgaa tatcttatga attaaggcat tcctctttcc    5100
ctaaccccga tggctccatt cccaagtacc ccaactcact gctgatccta ttaaaggaat    5160
gagtcctgct acccgagtgg tagtcatagc cctagatgac tctcaactac tcttcaaagg    5220
gaggcatcag gaatagaatg aaactgtgtg aaggataaga ttgttcgcat caagatccaa    5280
atcttgattt catattaacg cctaaggatt gcctgtgtgc tggaaatata tttgaaactc    5340
aaccagtatg cccagcctat tgcatatcat tgtcagacca tttttgctgc tgtggtcacc    5400
cacgatttca tttgtcttat acccaggtga aggggaagg gtgaatggga ctggctggtt     5460
cctttaaatg ttaacttatg gaaatgctag ttcaaatggt aatgtcacag tgttttgtat    5520
gcagagagca agagttcaac caacagctgt ttattcatgt gtgtgtgtct ttgctgcttt    5580
gagttctctg tatctactgt gtatgtgaat ggtcatgtgg gactcagtgg tggtgttgtg    5640
actttgacct agggtccgag tgtcacagct gatcttggca ctcggcactc attggcacag    5700
tggtagttag aggtgaaaag tagagctgtc aagcccaagg gcttagcttt agggctcctc    5760
ctgagttcgg cccacagtag aagcaagatt ttaactagcc ccttttcctc ttcaccctcc    5820
catgatgcgc agtgttcaga aagctggtaa gtcctaggga tttccagaag tagcctgcag    5880
aagaaggtaa gtttgaaagc cactccaggg gtcctgatgc tgtcatgctc agtgagccat    5940
tttacagttc tccaaagtct agccctgttt cggacctgca cttcacctct aagttatgta    6000
caactcaacc tgcatccctc taaaagtcct atatccatat tcaccattgg ctaatttgag    6060
gccctgagtg ggccttgaat gctaaaaaga agcagggtac gcagggctac atgtagatac    6120
cacaccaagg ctggaggctg gtctgtcata agacagaaag aaagacgctg ggcccaattt    6180
tgacttggcc aggggacacc ttggtgtgtt tgttatcttt atctgtgggt aggctagctg    6240
acccatctcc ttgagtcatt cccttttggga accccactg ccagtattga tctcctttt    6300 gccttgtact gaatgacaca ttacctccac actctcccgg actaggtggt caacagggcc    6360
acagggttgc tttctgtctt tggtggggca ggggagttga cagggatgag ggtccaagga    6420
ataagcatga atgacaagaa aacaagggaa agagttaacc tgtcacatag caggttaact    6480
ttttcagggt ttgcagttag aggtattcga ccattcactg gctgagccag atcacgggaa    6540
cttgagagct tttactgtga ttcttcaatg taaaaaataa acaacaatgt caaactgtgt    6600
ttatatgatt tgtataaagc cttttttaaga ttactattta aataaacatt ataccagaga    6660
taaaaaaaaa a                                                         6671
```

<210> SEQ ID NO 23
<211> LENGTH: 931
<212> TYPE: PRT
<213> ORGANISM: Homo sapiens

<400> SEQUENCE: 23

```
Met Asp Met Phe Pro Leu Thr Trp Val Phe Leu Ala Leu Tyr Phe Ser
1               5                   10                  15

Arg His Gln Val Arg Gly Gln Pro Asp Pro Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80
```

```
His Asp Cys Lys Tyr Asp Phe Ile Glu Ile Arg Asp Gly Asp Ser Glu
             85                  90                  95

Ser Ala Asp Leu Leu Gly Lys His Cys Gly Asn Ile Ala Pro Pro Thr
        100                 105                 110

Ile Ile Ser Ser Gly Ser Met Leu Tyr Ile Lys Phe Thr Ser Asp Tyr
            115                 120                 125

Ala Arg Gln Gly Ala Gly Phe Ser Leu Arg Tyr Glu Ile Phe Lys Thr
        130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
        210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
        290                 295                 300

Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
            340                 345                 350

Gln Asn Gly Tyr Tyr Val Lys Ser Tyr Lys Leu Glu Val Ser Thr Asn
        355                 360                 365

Gly Glu Asp Trp Met Val Tyr Arg His Gly Lys Asn His Lys Val Phe
        370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
            420                 425                 430

Pro Cys Ser Asn Met Leu Gly Met Leu Ser Gly Leu Ile Ala Asp Ser
        435                 440                 445

Gln Ile Ser Ala Ser Ser Thr Gln Glu Tyr Leu Trp Ser Pro Ser Ala
        450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
```

-continued

```
                500             505             510
    Thr Ala Val Glu Ala Arg Ala Phe Val Arg Lys Phe Lys Val Ser Tyr
                    515             520             525

Ser Leu Asn Gly Lys Asp Trp Glu Tyr Ile Gln Asp Pro Arg Thr Gln
                530             535             540

Gln Pro Lys Leu Phe Glu Gly Asn Met His Tyr Asp Thr Pro Asp Ile
    545             550             555             560

Arg Arg Phe Asp Pro Ile Pro Ala Gln Tyr Val Arg Val Tyr Pro Glu
                        565             570             575

Arg Trp Ser Pro Ala Gly Ile Gly Met Arg Leu Glu Val Leu Gly Cys
                    580             585             590

Asp Trp Thr Asp Ser Lys Pro Thr Val Glu Thr Leu Gly Pro Thr Val
                595             600             605

Lys Ser Glu Glu Thr Thr Thr Pro Tyr Pro Thr Glu Glu Glu Ala Thr
                    610             615             620

Glu Cys Gly Glu Asn Cys Ser Phe Glu Asp Asp Lys Asp Leu Gln Leu
    625             630             635             640

Pro Ser Gly Phe Asn Cys Asn Phe Asp Phe Leu Glu Glu Pro Cys Gly
                        645             650             655

Trp Met Tyr Asp His Ala Lys Trp Leu Arg Thr Thr Trp Ala Ser Ser
                    660             665             670

Ser Ser Pro Asn Asp Arg Thr Phe Pro Asp Asp Arg Asn Phe Leu Arg
                675             680             685

Leu Gln Ser Asp Ser Gln Arg Glu Gly Gln Tyr Ala Arg Leu Ile Ser
                    690             695             700

Pro Pro Val His Leu Pro Arg Ser Pro Val Cys Met Glu Phe Gln Tyr
    705             710             715             720

Gln Ala Thr Gly Gly Arg Gly Val Ala Leu Gln Val Val Arg Glu Ala
                        725             730             735

Ser Gln Glu Ser Lys Leu Leu Trp Val Ile Arg Glu Asp Gln Gly Gly
                    740             745             750

Glu Trp Lys His Gly Arg Ile Ile Leu Pro Ser Tyr Asp Met Glu Tyr
                755             760             765

Gln Ile Val Phe Glu Gly Val Ile Gly Lys Gly Arg Ser Gly Glu Ile
                    770             775             780

Ala Ile Asp Asp Ile Arg Ile Ser Thr Asp Val Pro Leu Glu Asn Cys
    785             790             795             800

Met Glu Pro Ile Ser Ala Phe Ala Gly Glu Asn Phe Lys Val Asp Ile
                        805             810             815

Pro Glu Ile His Glu Arg Glu Gly Tyr Glu Asp Glu Ile Asp Asp Glu
                    820             825             830

Tyr Glu Val Asp Trp Ser Asn Ser Ser Ser Ala Thr Ser Gly Ser Gly
                835             840             845

Ala Pro Ser Thr Asp Lys Glu Lys Ser Trp Leu Tyr Thr Leu Asp Pro
    850             855             860

Ile Leu Ile Thr Ile Ile Ala Met Ser Ser Leu Gly Val Leu Leu Gly
                        865             870             875             880

Ala Thr Cys Ala Gly Leu Leu Leu Tyr Cys Thr Cys Ser Tyr Ser Gly
                    885             890             895

Leu Ser Ser Arg Ser Cys Thr Thr Leu Glu Asn Tyr Asn Phe Glu Leu
                900             905             910

Tyr Asp Gly Leu Lys His Lys Val Lys Met Asn His Gln Lys Cys Cys
                    915             920             925
```

Ser Glu Ala
    930

<210> SEQ ID NO 24
<211> LENGTH: 1524
<212> TYPE: DNA
<213> ORGANISM: Homo sapiens

<400> SEQUENCE: 24

| | | | | | |
|---|---|---|---|---|---|
| agcagacaga | ggactctcat | taaggaaggt | gtcctgtgcc | ctgaccctac | aagatgccaa | 60 |
| gagaagatgc | tcacttcatc | tatggttacc | ccaagaaggg | gcacggccac | tcttacacca | 120 |
| cggctgaaga | ggccgctggg | atcggcatcc | tgacagtgat | cctgggagtc | ttactgctca | 180 |
| tcggctgttg | gtattgtaga | agacgaaatg | gatacagagc | cttgatggat | aaaagtcttc | 240 |
| atgttggcac | tcaatgtgcc | ttaacaagaa | gatgcccaca | agaagggttt | gatcatcggg | 300 |
| acagcaaagt | gtctcttcaa | gagaaaaact | gtgaacctgt | ggttcccaat | gctccacctg | 360 |
| cttatgagaa | actctctgca | gaacagtcac | caccacctta | ttcaccttaa | gagccagcga | 420 |
| gacacctgag | acatgctgaa | attatttctc | tcacactttt | gcttgaattt | aatacagaca | 480 |
| tctaatgttc | tcctttggaa | tggtgtagga | aaaatgcaag | ccatctctaa | taataagtca | 540 |
| gtgttaaaat | tttagtaggt | ccgctagcag | tactaatcat | gtgaggaaat | gatgagaaat | 600 |
| attaaattgg | gaaaactcca | tcaataaatg | ttgcaatgca | tgatactatc | tgtgccagag | 660 |
| gtaatgttag | taaatccatg | gtgttatttt | ctgagagaca | gaattcaagt | gggtattctg | 720 |
| gggccatcca | atttctcttt | acttgaaatt | tggctaataa | caaactagtc | aggttttcga | 780 |
| accttgaccg | acatgaactg | tacacagaat | tgttccagta | ctatggagtg | ctcacaaagg | 840 |
| atacttttac | aggttaagac | aaaggggttga | ctggcctatt | tatctgatca | agaacatgtc | 900 |
| agcaatgtct | ctttgtgctc | taaaattcta | ttatactaca | ataatatatt | gtaaagatcc | 960 |
| tatagctctt | ttttttgag | atggagtttc | gcttttgttg | cccaggctgg | agtgcaatgg | 1020 |
| cgcgatcttg | gctcaccata | acctccgcct | cccaggttca | agcaattctc | ctgccttagc | 1080 |
| ctcctgagta | gctgggatta | caggcgtgcg | ccactatgcc | tgactaattt | tgtagtttta | 1140 |
| gtagagacgg | ggtttctcca | tgttggtcag | gctggtctca | aactcctgac | ctcaggtgat | 1200 |
| ctgcccgcct | cagcctccca | aagtgctgga | attacaggcg | tgagccacca | cgcctggctg | 1260 |
| gatcctatat | cttaggtaag | acatataacg | cagtctaatt | acatttcact | tcaaggctca | 1320 |
| atgctattct | aactaatgac | aagtattttc | tactaaacca | gaaattggta | gaaggattta | 1380 |
| aataagtaaa | agctactatg | tactgcctta | gtgctgatgc | ctgtgtactg | ccttaaatgt | 1440 |
| acctatggca | atttagctct | cttgggttcc | caaatccctc | tcacaagaat | gtgcagaaga | 1500 |
| aatcataaag | gatcagagat | tctg | | | | 1524 |

<210> SEQ ID NO 25
<211> LENGTH: 118
<212> TYPE: PRT
<213> ORGANISM: Homo sapiens

<400> SEQUENCE: 25

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys

```
                35                  40                  45
Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Ala Tyr Glu Lys Leu Ser Ala Glu Gln Ser
            100                 105                 110

Pro Pro Pro Tyr Ser Pro
            115
```

ASSAYS AND METHODS RELATING TO THE TREATMENT OF MELANOMA

CROSS-REFERENCE TO RELATED APPLICATIONS

This application is a 35 U.S.C. § 371 National Phase Entry Application of International Application No. PCT/US2014/071456 filed Dec. 19, 2014, which designates the U.S. and claims benefit under 35 U.S.C. § 119(e) of U.S. Provisional Application No. 61/919,064 filed Dec. 20, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 11, 2014, is named 701586-078961-PCT_SL.txt and is 24,130 bytes in size.

TECHNICAL FIELD

The technology described herein relates to the prognosis and treatment of melanoma.

BACKGROUND

Patients with advanced melanoma experience a high mortality rate (Balch et al. J Clin Oncol. 2009 Dec. 20; 27(36):6199-206). Currently, the standard method of treatment is early diagnosis followed by appropriate complete surgical excision. Additional treatments are available for high-risk patients, but accurate methods of identifying such patients are not currently available in the clinic (Bhatia et al. Oncology. 2009 23(6):488-96; Nashan et al. J Eur Acad Dermatol Venereol. 2007 21(10):1305-18; and Nathanson K L. Biochemical pharmacology. 2010 80(5):755-61).

Improved diagnostic and prognostic tools for melanoma are further complicated by the fact that many tissue samples, particularly archival tissue samples are FFPE (formalin-fixed paraffin-embedded) samples. Quantitative assessments of gene expression in FFPE samples are challenging because RNA extracted from FFPE samples exists as fragments less than 300 bases in length.

SUMMARY

Traditional histological examination of melanoma lesions at the time of diagnosis cannot accurately predict which melanomas will exhibit aggressive behavior, particular metastasis. As described herein, the inventors have discovered that the ratio of the expression of NRP-2:Melan-A in melanoma cells is an accurate predictor of whether or not the melanoma is potentially metastatic. Accordingly, provided herein are methods for measuring this ratio and methods of treatment of melanoma.

In one aspect, described herein is an assay for detecting a malignant melanoma, the assay comprising: (a) measuring the level of neurophilin-2 (NRP-2) mRNA in a sample obtained from a subject with melanoma; (b) measuring the level of Melan-A (MART) mRNA in the sample obtained from the subject; and (c) calculating the value of NRP-2:MART from the levels obtained in steps (a) and (b); wherein malignant melanoma is detected in the sample if the value of NRP-2:MART is increased relative to a reference level. In some embodiments, the sample is an FFPE sample. In some embodiments, the levels of the mRNAs are measured using quantitative RT-PCR. In some embodiments, amplicons of less than 150 bp are amplified during PCR. In some embodiments, amplicons of less than 100 bp are amplified during PCR. In some embodiments, a known quantity of an internal control nucleic acid is added to the sample prior to measuring the level of NRP-2 and Melan-A mRNAs. In some embodiments, steps (a) and (b) comprise performing duplex RT-PCR wherein the level of the internal control nucleic acid is measured simultaneously with the measurement of NRP-2 and Melan-A mRNAs. In some embodiments, the level of NRP-2 or Melan-A is normalized to the level of the internal control nucleic acid prior to performing step (c). In some embodiments, PCR is performed using one or more primers having the sequence of any of SEQ ID NOs: 1-2, 7-8, and 10-11. In some embodiments, the level of amplicons resulting from PCR is detected using one or more probes having the sequence of any of SEQ ID NOs: 3, 9, and 12. In some embodiments, the primers or probes are present in a reaction mixture at about the concentrations shown in Table 1. In some embodiments, the assay further comprises performing PCR using known quantities of NRP-2 and Melan-A nucleic acids to generate a standard curve; and calculating copy numbers of NRP-2 and Melan-A in the sample using the standard curve.

In one aspect, described herein is a method of treatment for melanoma, the method comprising: (a) measuring the level of neurophilin-2 (NRP-2) mRNA in a sample obtained from a subject with melanoma; (b) measuring the level of Melan-A (MART) mRNA in the sample obtained from the subject; (c) calculating the value of NRP-2:MART from the levels obtained in steps (a) and (b); and (d) surgically removing the melanoma and administering adjuvant therapy and follow-up monitoring if the value of NRP-2:MART is increased relative to a reference level; and not administering adjuvant therapy if the value of NRP-2:MART is not increased relative to a reference level. In some embodiments, the sample is an FFPE sample. In some embodiments, the levels of the mRNAs are measured using quantitative RT-PCR. In some embodiments, amplicons of less than 150 bp are amplified during PCR. In some embodiments, amplicons of less than 100 bp are amplified during PCR. In some embodiments, a known quantity of an internal control nucleic acid is added to the sample prior to measuring the level of NRP-2 and Melan-A mRNAs. In some embodiments, steps (a) and (b) comprise performing duplex RT-PCR wherein the level of the internal control nucleic acid is measured simultaneously with the measurement of NRP-2 and Melan-A mRNAs. In some embodiments, the level of NRP-2 or Melan-A is normalized to the level of the internal control nucleic acid prior to performing step (c). In some embodiments, PCR is performed using one or more primers having the sequence of any of SEQ ID NOs: 1-2, 7-8, and 10-11. In some embodiments, the level of amplicons resulting from PCR is detected using one or more probes having the sequence of any of SEQ ID NOs: 3, 9, and 12. In some embodiments, the primers or probes are present in a reaction mixture at about the concentrations shown in Table 1. In some embodiments, the method further comprises performing PCR using known quantities of NRP-2 and Melan-A nucleic acids to generate a standard curve; and calculating copy numbers of NRP-2 and Melan-A in the sample using the standard curve.

In one aspect, described herein is an assay for detecting a predisposition for a melanoma to become malignant, the assay comprising: (a) measuring the level of neurophilin-2

(NRP-2) mRNA in a sample obtained from a subject with melanoma; (b) measuring the level of Melan-A (MART) mRNA in the sample obtained from the subject; and (c) calculating the value of NRP-2:MART from the levels obtained in steps (a) and (b); wherein the melanoma is determined to have a predisposition to become malignant if the value of NRP-2:MART is increased relative to a reference level. In some embodiments, the sample is an FFPE sample. In some embodiments, the levels of the mRNAs are measured using quantitative RT-PCR. In some embodiments, amplicons of less than 150 bp are amplified during PCR. In some embodiments, amplicons of less than 100 bp are amplified during PCR. In some embodiments, a known quantity of an internal control nucleic acid is added to the sample prior to measuring the level of NRP-2 and Melan-A mRNAs. In some embodiments, steps (a) and (b) comprise performing duplex RT-PCR wherein the level of the internal control nucleic acid is measured simultaneously with the measurement of NRP-2 and Melan-A mRNAs. In some embodiments, the level of NRP-2 or Melan-A is normalized to the level of the internal control nucleic acid prior to performing step (c). In some embodiments, PCR is performed using one or more primers having the sequence of any of SEQ ID NOs: 1-2, 7-8, and 10-11. In some embodiments, the level of amplicons resulting from PCR is detected using one or more probes having the sequence of any of SEQ ID NOs: 3, 9, and 12. In some embodiments, the primers or probes are present in a reaction mixture at about the concentrations shown in Table 1. In some embodiments, the assay further comprises performing PCR using known quantities of NRP-2 and Melan-A nucleic acids to generate a standard curve; and calculating copy numbers of NRP-2 and Melan-A in the sample using the standard curve.

BRIEF DESCRIPTION OF THE DRAWINGS

FIGS. 1A-1C demonstrate NRP2 gene expression patterns in archival FFPE tissue specimens obtained from patients with nevi, primary melanomas, and metastases. Box plots of quantitative mRNA expression level for NRP2 (FIG. 1A) and ACTB (FIG. 1B) genes in sample groups of nevi, primary, and metastases. ACTB gene serves as a negative control. ANOVA results show mRNA expression level for NRP2 is significantly greater in metastatic group (p-value based on Tukey-Kramer test). Scatter plots of NRP2 gene transcript copy numbers with Breslow depth in primary melanomas FIG. 1C depicts a graph of Pearson correlation analysis demonstrating that gene expression levels of NRP2 are highly correlated with Breslow depth of early stage primary melanomas.

FIG. 3 depicts a table of the clinical characteristics of the patient groups with primary melanoma, metastasis, and nevus used in the NRP2 expression analysis of FFPE tissue.

FIG. 4A depicts a box plot analysis of two independent sets of patient tissue samples. NRP2 expression levels were measured by qRT-PCR as described elsewhere herein (Rossi et al. BJD 2014). For data points of the three groups designated as "Naevi", "Primary", and "Met", p=0.00176 from ANOVA test for the three groups. The data point of "Benign" and "Malignant" were generated with a separate set of patient samples. NRP2 expression in "Benign" is significantly different than that of and "Malignant" with p=0.003704 from Two Sample t-test. FIG. 4B depicts a boxplot of "Naevi" and "Benign" from FIG. 4A combined as "Benign"; "Primary", "Met", and "Malignant" from FIG. 4A are combined as "Malignant".

FIG. 6A depicts scatter plots of NRP2 gene expression (hybridization units from microarray profile dataset) with Breslow depth in primary melanomas (Breslow depth of <14.4 mm including two melanoma in situ, n=14) FIG. 6B depicts pearson correlation analysis indicating significant correlation of NRP2 gene expression with Breslow depth in primary melanomas. Detailed descriptions regarding the composition of the patient cohort can be found in the Gene Expression Omnibus (GEO), a National Institutes of Health funded microarray data deposition website (available on the World Wide Web at.ncbi.nlm.nih.gov/geo). GEO accession number is GSE7553.

FIG. 7 depicts a table of clinical characteristics of the patient groups with primary melanoma, metastasis, and naevus used in the NPR2 expression analysis of FFPE tissue samples.

DETAILED DESCRIPTION

Figure 2:
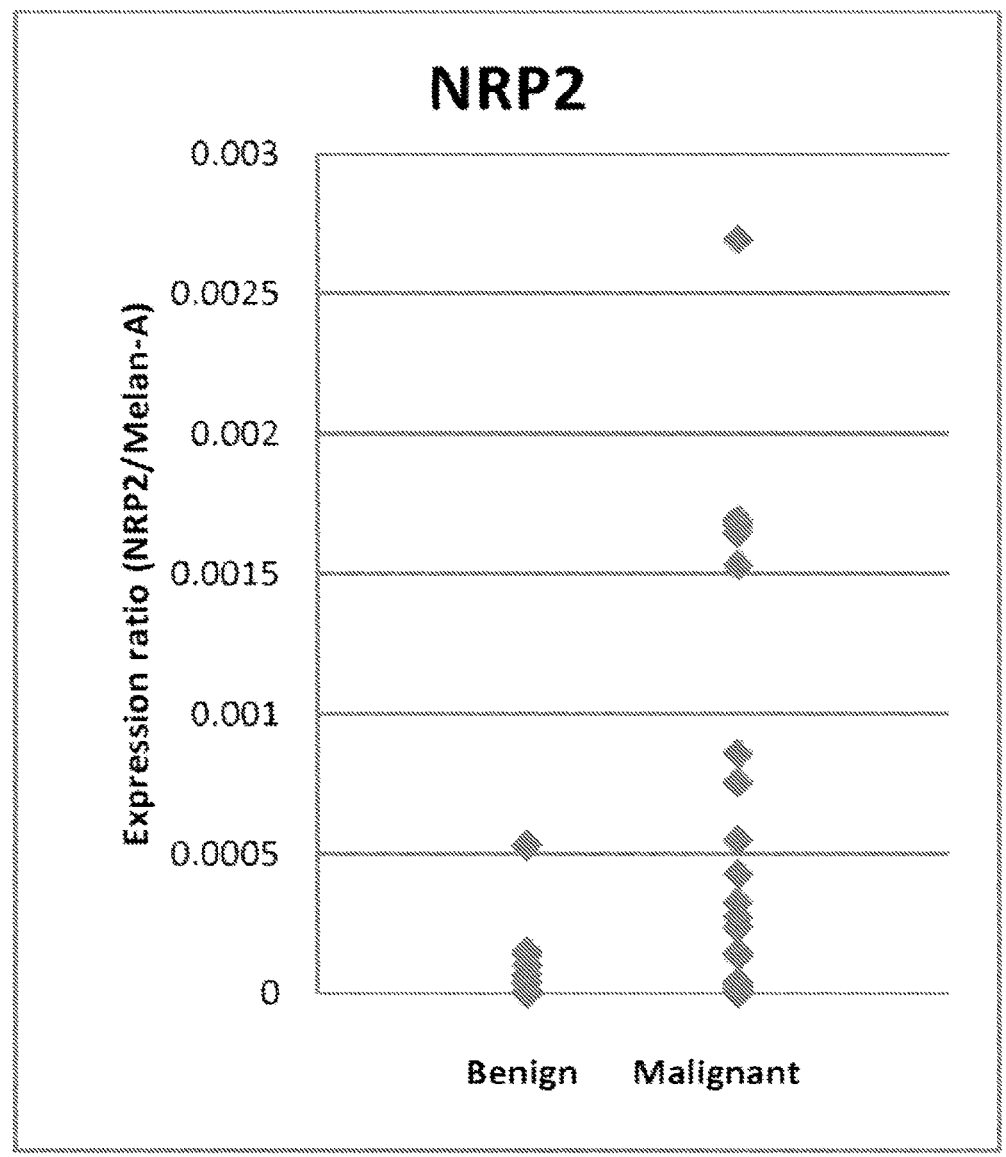
FIG. 2 demonstrates that expression ratio of NRP2 and melan-A gene transcript copy numbers are segregated between two groups of melanoma patient groups, benign (n=15) and malignant (n=21). Statistical analysis (student t-test) shows the significant difference between the two groups (p-value 0.0038).

As described herein, the inventors have discovered that the ratio of NRP-2:Melan-A gene expression is an accurate predictor of whether or not a melanoma is or will become metastatic. This is in contrast to the absolute level of NRP-2, or NRP-2 as normalized to other genes, which does not provide the accuracy and reliability of the methods and assays described herein. Accordingly, provided herein are assays and methods relating to measuring the ratio of NRP-2:Melan-A to diagnose, prognose, or treat melanoma.

While the a correlation of NRP-2 expression may be a natural phenomemon, the technology described herein relates to a practical application of such a correlation, and involves assays and methods directed specifically to NRP-2 mRNA levels as normalized to MART. These assays and methods provide a specificity, accuracy, and quantitative nature not found by examination of NRP-2 expression measured by other methods. Accordingly, the assays and methods described herein are significantly different than a mere assertion that NRP-2 is correlated with melanoma.

As used herein, "NRP-2" or "neuropilin-2" refers to a transmembrane glycoprotein receptor which recognizes class 3 semaphorins and VEGF. NRPs regulate axon growth and angiogensis. NRP2 can be distinguished from NRP1 in that NRP2 has a higher affinity for Sema-3F rather than Sema-3A. The sequences of NRP-2 genes, transcripts, and polypeptides are known in a variety of species, e.g. human NRP-2 mRNA (e.g. SEQ ID NO: 22; NCBI Ref Seq: NM_201266) and polypeptide (e.g. SEQ ID NO: 023; NCBI Ref Seq: NP_957718) sequences (NCBI Gene ID: 8828).

As used herein, "Melan-A" or "MART-1" refers to a transmembrane protein which is specific to the melanocyte cell lineage. Amino acids 27 to 35 of the protein can be presented to T cells via the MHC class I complex. The sequences of Melan-A genes, transcripts, and polypeptides are known in a variety of species, e.g. human Melan-A mRNA (e.g. SEQ ID NO: 24; NCBI Ref Seq: NM_005511) and polypeptide (e.g. SEQ ID NO: 025; NCBI Ref Seq: NP_005502) sequences (NCBI Gene ID: 2315).

In one aspect, provided herein is an assay for detecting a malignant melanoma, the assay comprising (a) measuring the level of neurophilin-2 (NRP-2) gene expression product in a sample obtained from a subject with melanoma; (b) measuring the level of Melan-A (MART) gene expression product in the sample obtained from the subject; and (c) calculating the value of NRP-2:MART from the levels obtained in steps (a) and (b); wherein malignant melanoma is detected in the sample if the value of NRP-2:MART is increased relative to a reference level. In some embodiments, the gene expression product can be, e.g. a polypeptide or mRNA. In some embodiments, the gene expression product can be an mRNA.

An increase relative to a reference level can be a level which is at least about 10% greater than the reference level, at least about 20%, at least about 30%, at least about 40%, at least about 50%, at least about 75%, at least about 100%, at least about 200%, at least about 300%, at least about 400%, at least about 500%, at least about 1000% greater than the reference level or greater. In some embodiments, an increase relative to a reference level can be a level which is statistically significantly greater than the reference level.

In some embodiments, an increase relative to a reference level which indicates treatment in accordance to the methods described herein is needed, or indicates a risk of metastatic melanoma is a level which is at least 2 σ greater than a reference level, e.g. 2 σ, 3 σ, or 4σ or greater than the reference level. As used herein "σ" or "standard deviation" refers to a measure of the amount of variation or dispersion from the average in a population.

In some embodiments, measuring the level of a gene expression product can comprise transforming the gene expression product into a detectable molecule and measuring the amount of the detectable molecule, e.g. amplifying an amplicon during RT-PCR, or hybridizing an mRNA with a detectable probe.

In some embodiments, the reference level can comprise the level of NRP-2:Melan-A in a sample of the same type taken from a subject not exhibiting any signs or symptoms of a melanoma. In some embodiments, the reference level can comprise the level of NRP-2:Melan-A in a sample of the same type taken from a subject not having or diagnosed as having melanoma. In some embodiments, the reference level can comprise the level of NRP-2:Melan-A in a melanocyte not exhibiting any signs of cancer. In some embodiments, the reference level can comprise the level of NRP-2:Melan-A in a sample of the same type taken from a subject whose melanoma did not exhibit metastasis. In some embodiments, the reference level can be the level in a sample of similar cell type, sample type, sample processing, and/or obtained from a subject of similar age, sex and other demographic parameters as the sample/subject for which the level of NRP-2:Melan-A is to be determined. In some embodiments, the test sample and control reference sample are of the same type, that is, obtained from the same biological source, and comprising the same composition, e.g. the same number and type of cells.

As used herein, the term "transforming" or "transformation" refers to changing an object or a substance, e.g., biological sample, nucleic acid or protein, into another substance. The transformation can be physical, biological or chemical. Exemplary physical transformation includes, but not limited to, pre-treatment of a biological sample, e.g., from whole blood to blood serum by differential centrifugation. A biological/chemical transformation can involve at least one enzyme and/or a chemical reagent in a reaction. For example, a nucleic acid sample can be digested into fragments by one or more restriction enzyme, or an exogenous molecule can be attached to a nucleic acid sample with a ligase. In some embodiments, a nucleic acid sample can undergo enzymatic replication, e.g., by polymerase chain reaction (PCR).

Methods to measure gene expression products associated with the genes described herein are well known to a skilled artisan. Such methods to measure gene expression products, e.g., protein level, include ELISA (enzyme linked immunosorbent assay), western blot, and immunoprecipitation, immunofluorescence using detection reagents such as an antibody or protein binding agents. Alternatively, a peptide can be detected in a subject by introducing into a subject a labeled anti-peptide antibody and other types of detection agent. For example, the antibody can be labeled with a radioactive marker whose presence and location in the subject is detected by standard imaging techniques. In certain embodiments, the gene expression products as described herein can be instead determined by determining the level of messenger RNA (mRNA) expression of NRP-2 and/or Melan-A as described herein. Such molecules can be isolated, derived, or amplified from a biological sample, such as a tumor biopsy. Detection of mRNA expression is known by persons skilled in the art, and comprise, for example but not limited to, PCR procedures, RT-PCR, Northern blot analysis, differential gene expression, RNA protection assay, microarray analysis, hybridization methods etc. In some embodiments, the level of the mRNAs can be measured using quantitative RT-PCR.

In general, the PCR procedure describes a method of gene amplification which is comprised of (i) sequence-specific hybridization of primers to specific genes or sequences within a nucleic acid sample or library, (ii) subsequent amplification involving multiple rounds of annealing, elongation, and denaturation using a thermostable DNA polymerase, and (iii) screening the PCR products for a band of the correct size. The primers used are oligonucleotides of sufficient length and appropriate sequence to provide initiation of polymerization, i.e. each primer is specifically designed to be complementary to a strand of the genomic locus to be amplified. In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

The nucleic acid sequences of the genes described herein have been assigned NCBI accession numbers for different species such as human, mouse and rat. In particular, the NCBI accession numbers for the nuclei acid sequences of the human genes are included herein (e.g. SEQ ID NOs: 22 and 24). Accordingly, a skilled artisan can design an appropriate primer based on the known sequence for determining the mRNA level of the respective gene.

Nucleic acid and ribonucleic acid (RNA) molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (Roiff, A et al. PCR: Clinical Diagnostics and Research, Springer (1994)).

In general, the PCR procedure describes a method of gene amplification which is comprised of (i) sequence-specific hybridization of primers to specific genes within a nucleic acid sample or library, (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

In an alternative embodiment, mRNA level of gene expression products described herein can be determined by reverse-transcription (RT) PCR and by quantitative RT-PCR (QRT-PCR) or real-time PCR methods. Methods of RT-PCR and QRT-PCR are well known in the art.

In some embodiments, one or more of the reagents (e.g. an antibody reagent and/or nucleic acid probe) described herein can comprise a detectable label and/or comprise the ability to generate a detectable signal (e.g. by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g. antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is label with a fluorescent compound. When the fluorescently labeled antibody is exposed to light of the proper wavelength, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoerythrin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. In some embodiments, a detectable label can be a radiolabel including, but not limited to $^{3}$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detectably label an antibody reagent include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. In some embodiments, a detectable label is a chemiluminescent label, including, but not limited to lucigenin, luminol, luciferin, isoluminol, theromatic acridinium ester, imidazole, acridinium salt and oxalate ester. In some embodiments, a detectable label can be a spectral colorimetric label including, but not limited to colloidal gold or colored glass or plastic (e.g., polystyrene, polypropylene, and latex) beads.

In some embodiments, detection reagents can also be labeled with a detectable tag, such as c-Myc, HA, VSV-G, HSV, FLAG, V5, HIS, or biotin. A reagent can also be detectably labeled using fluorescence emitting metals such as $^{152}$Eu, or others of the lanthanide series. These metals can be attached to the reagent using such metal chelating groups as diethylenetriaminepentaacetic acid (DTPA) or ethylenediaminetetraacetic acid (EDTA).

In some embodiments, the amplicons amplified during PCR can be 300 bp or less, e.g. 300 bp or less, 200 bp or less, 150 bp or less, or 100 bp or less. In some embodiments, the amplicons amplified during PCR can be 150 bp or less. In some embodiments, the amplicons amplified during PCR can be 100 bp or less.

In some embodiments, the PCR reaction can be a duplex PCR reaction, e.g. the level of two target nucleic acids can be measured simultaneously in the same reaction mixture. In some embodiments, the PCR reaction can be a multiplex PCR reaction, e.g. the level of two or more target nucleic acids can be measured simultaneously in the same reaction mixture.

In some embodiments of any of the aspects described herein, the level of expression products of more than one gene can be determined simultaneously (e.g. a multiplex assay) or in parallel. In some embodiments, the level of expression products of no more than 200 other genes is determined. In some embodiments, the level of expression products of no more than 100 other genes is determined. In some embodiments, the level of expression products of no more than 20 other genes is determined. In some embodiments, the expression level of no more than 10 other genes is determined.

In some embodiments, an internal control can be added to the sample prior to the measuring step(s), e.g. a known amount of the internal control can be added. As used herein, "internal control" refers to a nucleic acid molecule which is not present in the sample in situ and the detection of which can control for variance in the PCR reaction, e.g. varying efficiencies or failed reactions as opposed to variances in the actual level of NRP-2 or Melan-A. In some embodiments, the level of NRP-2 and/or Melan-A can be normalized relative to the measured level (or to the ratio of detected vs. originally added) internal control. In some embodiments, this normalization is performed before step (c). Those of ordinary skill in the art are aware of methods of normalization.

The internal control can be, e.g. a DNA or a RNA, e.g. a mRNA. In some embodiments, the internal control can be added prior to a reverse transcriptase reaction. In some embodiments, the internal control can be after a reverse transcriptase reaction.

In some embodiments, the level of the internal control can be detected during PCR, e.g. in a duplex PCR reaction with either NRP-2 or Melan-A. In some embodiments, the level of the internal control can be measured simultaneously with the measurement of NRP-2 and/or Melan-A mRNA levels, e.g. steps (a) and (b) can further comprise measuring the level of the internal control.

In some embodiments, the internal control comprises a nucleic acid sequence which is not found in the sample, e.g. a nucleic acid sequence (e.g. an RNA) not found in tumor cells, or human cells, or mammalian cells. In some embodiments, the internal control can be a synthetic nucleic acid sequence. In some embodiments, the internal control can be a non-human nucleic acid sequence. In some embodiments, the internal control can be a non-mammalian nucleic acid sequence. In some embodiments, the internal control can be a luciferase nucleic acid.

Exemplary primers are described herein. By way of non-limiting example, primers having the sequence of one or more of SEQ ID NOs: 1-2, 7-8, and 10-11 can be used in the PCR reactions described herein. By way of further non-limiting example, probes having the sequence of one or more of SEQ ID NOs: 3, 9, and 12 can be used to detect amplicons resulting from PCR with, e.g. primers of SEQ ID NOs: 1-2, 7-8, and 10-11. In some embodiments, primers and/or probes can be present in a reaction mixture at about the concentrations shown in Table 1. Additional primers and probes can be readily designed using the exemplary sequences provided herein, e.g. by shortening or lengthening the primers or probes, or selecting alternative sequences from the mRNA (e.g. SEQ ID NO: 22 or 24) to which primers and/or probes can hybridize.

In some embodiments, the PCR reactions described above herein can additionally be performed with known quantitites of NRP-2 and/or Melan-A nucleic acids, e.g. multiple PCR reactions can be performed with multimple known quantities of NRP-2 and/or Melan-A nucleic acids, and a standard curve can be generated and/or calculated. The use of such standard curves, e.g. to correct for reaction efficiencies and accurately calculate the original amount of a target present in a sample is known in the art.

The term "sample" or "test sample" as used herein denotes a sample taken or isolated from a biological organism, e.g., a tumor sample from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "test sample" also includes untreated or pretreated (or pre-processed) biological samples. In some embodiments, a test sample can comprise cells from subject. In some embodiments, a test sample can be a tumor cell test sample, e.g. the sample can comprise cancerous cells, cells from a tumor, and/or a tumor biopsy.

The test sample can be obtained by removing a sample of cells from a subject, but can also be accomplished by using previously isolated cells (e.g. isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for measuring the level of mRNAs as described herein.

In some embodiments, the sample can be a tumor biopsy. In some embodiments, the sample can be a FFPE sample.

In some embodiments, the methods and assays described herein can further comprise a step of obtaining a test sample from a subject. In some embodiments, the subject can be a human subject. In some embodiments, the subject can be a subject having or diagnosed as having melanoma. In some embodiments, the subject can be a subject at risk of having melanoma, e.g. a subject with new pigmented skin growths.

In one aspect, described herein is an assay for detecting a predisposition for a melanoma to become malignant, the assay comprising (a) measuring the level of neurophilin-2 (NRP-2) mRNA in a sample obtained from a subject with melanoma; (b) measuring the level of Melan-A (MART) mRNA in the sample obtained from the subject; and (c) calculating the value of NRP-2:MART from the levels obtained in steps (a) and (b); wherein the melanoma is determined to have a predisposition to become malignant if the value of NRP-2:MART is increased relative to a reference level. In one aspect, described herein is a method for detecting a predisposition for a melanoma to become malignant, the method comprising (a) measuring the level of neurophilin-2 (NRP-2) mRNA in a sample obtained from a subject with melanoma; (b) measuring the level of Melan-A (MART) mRNA in the sample obtained from the subject; and (c) calculating the value of NRP-2:MART from the levels obtained in steps (a) and (b); (d) determining that the melanoma is predisposed to become malignant if the value of NRP-2:MART is increased relative to a reference level. A melanoma predisposed to become malignant can be a melanoma with a greater likelihood or at greater risk to become malignant, as compared to a reference level. As used herein a "greater risk" or "greater likelihood" refers to at least a 2-fold greater likelihood or risk of being or becoming malignant than the risk level of a subject determined not to have an increased ratio of NRP-2:Melan-A according to an assay or method described herein, e.g. a 2-fold, or 2.5-fold, or 3-fold, or 4-fold, or greater risk.

In one aspect, described herein is a method of treatment for melanoma, the method comprising (a) measuring the level of neurophilin-2 (NRP-2) mRNA in a sample obtained from a subject with melanoma; (b) measuring the level of Melan-A (MART) mRNA in the sample obtained from the subject; (c) calculating the value of NRP-2:MART from the levels obtained in steps (a) and (b); and (d) administering a treatment for a malignant melanoma. In some embodiments, a treatment for a malignant melanoma can comprise surgically removing the melanoma and administering adjuvant therapy. In some embodiments, adjuvant therapy can comprise administration of, e.g. interferon, interleukin-2 (PROLEUKIN), and/or ipilimumab (YERVOY). In some embodiments, a treatment for a malignant melanoma can further comprise follow-up monitoring, e.g. closer follow-up monitoring than a low-risk patient would receive.

In some embodiments, the methods described herein relate to treating a subject having or diagnosed as having melanoma. Subjects having melanoma can be identified by a physician using current methods of diagnosing melanoma. Symptoms and/or complications of melanoma which characterize these conditions and aid in diagnosis are well known in the art and include but are not limited to, a change in an existing mole or the development of a new, usually pigmented skin growth. Tests that may aid in a diagnosis of, e.g. melanoma include, but are not limited to, examination of the skin, biopsy, punch biopsy, excision biopsy, incisional biopsy immunohistochemical examination of biopsies, measuring the thickness of the melanoma, sentinel node biopsy, X-ray, CT scan, MRI, PET, CT, ultrasound, LDH testing, and/or photoacoustic detection. A family history of melanoma or exposure to risk factors for melanoma (e.g. high UV exposure) can also aid in determining if a subject is likely to have melanoma or in making a diagnosis of melanoma.

A non-malignant melanoma is typically treated by surgically remove the melanoma. Therapies for subjects with malignant melanoma are known in the art and include, but are not limited to surgical removal of the melanoma, surgical removal of lymph nodes (particularly those nearest the melanoma or sentinel lymph nodes), chemotherapy (e.g. dacarbazine), radiation therapy, adjuvant therapy, (e.g. interferon, interleukin-2 (PROLEUKIN), and/or ipilimumab (YERVOY)), vemurafenib (ZELBORAF), and/or temozolomide. Any of the foregoing therapies for malignant melanoma can be administered according to the methods of treatment described herein.

In some embodiments of the various aspects described herein, the assay or method further comprises measuring the level of one or more marker genes selected from the group consisting of: IL8 (NCBI Ref Seq; 3576); AREG (NCBI Ref Seq; 374); MMP1 (NCBI Ref Seq; 4312); CSPG2 (NCBI Ref Seq; 1462); SerpinB2 (NCBI Ref Seq; 5055); RAP1A (NCBI Ref Seq; 5906); FLRT3 (NCBI Ref Seq; 23767); COL4A1 (NCBI Ref Seq; 1282); TK1 (NCBI Ref Seq; 7083); DHFR (NCBI Ref Seq; 1719); CDH3 (NCBI Ref Seq; 1001); HELLS (NCBI Ref Seq; 3070); KIT (NCBI Ref Seq; 3815); CXCL1 (NCBI Ref Seq; 2919); Ki67 (NCBI Ref Seq; 4288); MITF (NCBI Ref Seq; 4286); p53 (NCBI Ref Seq; 7157); and p21 (NCBI Ref Seq; 1026). An increase in the expression of the marker gene (e.g. the mRNA level) relative to a reference level indicates malignant melanoma is detected in the sample or that the melanoma has a predisposition to become malignant. The sequences of gene expression products of the foregoing genes are known, see, e.g. the NCBI entries for the given Ref Seq numbers, and one of skill in the art can readily design primer to detect and/or measure expression product levels. In some embodiments, the level of the expression product can be normalized, e.g. to MART.

In one aspect, described herein is a kit for performing an assay or method as described herein. In some embodiments, the kit can comprise a primer having the sequence of any of SEQ ID NOs: 1-2, 7-8 or 10-11 and/or a probe having the sequence of any of SEQ ID NOs: 3, 9, and 12. A kit is any manufacture (e.g., a package or container) comprising at least one reagent, e.g., a primer or probe, the manufacture being promoted, distributed, or sold as a unit for performing the methods described herein.

The kits described herein can optionally comprise additional components useful for performing the methods described herein. By way of example, the kit can comprise fluids (e.g., buffers) suitable for composition comprising primer or probe as described herein, an instructional material which describes performance of a method as described herein, and the like. A kit can further comprise devices and/or reagents for use of the primers or probes as described herein. Additionally, the kit may comprise an instruction leaflet and/or may provide information as to the relevance of the obtained results.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of melanoma. A subject can be male or female.

The term "melanoma" refers to a type of skin cancer. Among cells composing skin, melanin-pigment producing cells are referred to as melanocytes. When these cells become cancerous, the cancer is referred to as a melanoma. Melanoma can also form, rarely, in the eyes or internal organs.

The term "malignant" refers to a tumor or cancer that is metastatic, invades contiguous tissue, or is no longer under normal cellular growth control.

A "cancer" or "tumor" as used herein refers to an uncontrolled growth of cells which interferes with the normal functioning of the bodily organs and systems. A subject that has a cancer or a tumor is a subject having objectively measurable cancer cells present in the subject's body. Included in this definition are benign and malignant cancers, as well as dormant tumors or micrometastatses. Cancers which migrate from their original location and seed vital organs can eventually lead to the death of the subject through the functional deterioration of the affected organs. In some embodiments, a cancer cell can be a cell obtained from a tumor. By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant. Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

A subject can be one who has been previously diagnosed with or identified as suffering from or having a condition in need of treatment (e.g. melanoma) or one or more complications related to such a condition, and optionally, have already undergone treatment for melanoma or the one or more complications related to melanoma. Alternatively, a subject can also be one who has not been previously diagnosed as having melanoma or one or more complications related to melanoma. For example, a subject can be one who exhibits one or more risk factors for melanoma or one or more complications related to melanoma or a subject who does not exhibit risk factors.

A "subject in need" of treatment for a particular condition can be a subject having that condition, diagnosed as having that condition, or at risk of developing that condition.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. melanoma. The term "treating" includes reducing or alleviating at least one adverse effect or symptom of a condition, disease or disorder associated with a melanoma. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8).

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. An assay for detecting a malignant melanoma, the assay comprising:
   (a) performing quantitative duplex RT-PCR on a sample obtained from a subject to measure:
      1) the level of neurophilin-2 (NRP-2) in the sample; and
      2) a known quantity of an internal control nucleic acid added to the sample; and normalizing the level of NRP-2 to the level of the internal control nucleic acid;
   (b) performing quantitative duplex RT-PCR on a sample obtained from a subject to measure:
      1) the level of melan-A (MART) in the sample; and
      2) a known quantity of an internal control nucleic acid added to the sample; and
   normalizing the level of MART to the level of the internal control nucleic acid;
   (c) calculating the value of NRP-2:MART from the levels obtained in steps (a) and (b); wherein malignant melanoma is detected in the sample if the value of NRP-2:MART is increased by at least 2 σ relative to a reference level.

2. A method of treatment for melanoma, the method comprising:
   (a) performing quantitative duplex RT-PCR on a sample obtained from a subject to measure:
      1) the level of neurophilin-2 (NRP-2) in the sample; and
      2) a known quantity of an internal control nucleic acid added to the sample; and
   normalizing the level of NRP-2 to the level of the internal control nucleic acid;
   (b) performing quantitative duplex RT-PCR on a sample obtained from a subject to measure:
      1) the level of melan-A (MART) in the sample; and
      2) a known quantity of an internal control nucleic acid added to the sample; and
   normalizing the level of MART to the level of the internal control nucleic acid;
   (c) calculating the value of NRP-2:MART from the levels obtained in steps (a) and (b); and
   (d) surgically removing the melanoma and administering adjuvant therapy and follow-up monitoring if the value of NRP-2:MART is increased at least 2 σ relative to a reference level; and not administering adjuvant therapy if the value of NRP-2:MART is not increased at least 2 σ relative to a reference level.

3. The assay or method of any of paragraphs 1-2, wherein PCR is performed using one or more primers having the sequence of any of SEQ ID NOs: 1-2, 7-8, and 10-11.

4. The assay or method of any of paragraphs 1-3, wherein the level of amplicons resulting from PCR is detected using one or more probes having the sequence of any of SEQ ID NOs: 3, 9, and 12.

5. The assay or method of any of paragraphs 1-4, wherein the primers or probes are present in a reaction mixture at about the concentrations shown in Table 1.

6. An assay for detecting a malignant melanoma, the assay comprising:
   (a) measuring the level of neurophilin-2 (NRP-2) mRNA in a sample obtained from a subject with melanoma;
   (b) measuring the level of Melan-A (MART) mRNA in the sample obtained from the subject; and
   (c) calculating the value of NRP-2:MART from the levels obtained in steps (a) and (b);
   wherein malignant melanoma is detected in the sample if the value of NRP-2:MART is increased relative to a reference level.

7. The assay of paragraph 6, wherein the sample is an FFPE sample.

8. The assay of any of paragraphs 6-7, wherein the levels of the mRNAs are measured using quantitative RT-PCR.

9. The assay of paragraph 8, wherein amplicons of less than 150 bp are amplified during PCR.

10. The assay of paragraph 8, wherein amplicons of less than 100 bp are amplified during PCR.

11. The assay of any of paragraphs 6-10, wherein a known quantity of an internal control nucleic acid is added to the sample prior to measuring the level of NRP-2 and Melan-A mRNAs.

12. The assay of any of paragraphs 6-11, wherein steps (a) and (b) comprise performing duplex RT-PCR wherein the level of the internal control nucleic acid is measured simultaneously with the measurement of NRP-2 and Melan-A mRNAs.

13. The assay of paragraph 12, wherein the level of NRP-2 or Melan-A is normalized to the level of the internal control nucleic acid prior to performing step (c).

14. The assay of any of paragraphs 6-13, wherein PCR is performed using one or more primers having the sequence of any of SEQ ID NOs: 1-2, 7-8, and 10-11.

15. The assay of any of paragraphs 6-14, wherein the level of amplicons resulting from PCR is detected using one or more probes having the sequence of any of SEQ ID NOs: 3, 9, and 12.

16. The assay of any of paragraphs 6-15, wherein the primers or probes are present in a reaction mixture at about the concentrations shown in Table 1.

17. The assay of any of paragraphs 6-16, further comprising
   performing PCR using known quantities of NRP-2 and Melan-A nucleic acids to generate a standard curve; and calculating copy numbers of NRP-2 and Melan-A in the sample using the standard curve.

18. A method of treatment for melanoma, the method comprising:
   (a) measuring the level of neurophilin-2 (NRP-2) mRNA in a sample obtained from a subject with melanoma;
   (b) measuring the level of Melan-A (MART) mRNA in the sample obtained from the subject;
   (c) calculating the value of NRP-2:MART from the levels obtained in steps (a) and (b); and
   (d) surgically removing the melanoma and administering adjuvant therapy and follow-up monitoring if the value of NRP-2:MART is increased relative to a reference level; and not administering adjuvant therapy if the value of NRP-2:MART is not increased relative to a reference level.

19. The method of paragraph 18, wherein the sample is an FFPE sample.

20. The method of any of paragraphs 18-19, wherein the levels of the mRNAs are measured using quantitative RT-PCR.

21. The method of paragraph 20, wherein amplicons of less than 150 bp are amplified during PCR.

22. The method of paragraph 20, wherein amplicons of less than 100 bp are amplified during PCR.

23. The method of any of paragraphs 18-22, wherein a known quantity of an internal control nucleic acid is added to the sample prior to measuring the level of NRP-2 and Melan-A mRNAs.

24. The method of any of paragraphs 18-23, wherein steps (a) and (b) comprise performing duplex RT-PCR wherein the level of the internal control nucleic acid is measured simultaneously with the measurement of NRP-2 and Melan-A mRNAs.

25. The method of paragraph 24, wherein the level of NRP-2 or Melan-A is normalized to the level of the internal control nucleic acid prior to performing step (c).

26. The method of any of paragraphs 18-25, wherein PCR is performed using one or more primers having the sequence of any of SEQ ID NOs: 1-2, 7-8, and 10-11.

27. The method of any of paragraphs 18-26, wherein the level of amplicons resulting from PCR is detected using one or more probes having the sequence of any of SEQ ID NOs: 3, 9, and 12.

28. The method of any of paragraphs 18-27, wherein the primers or probes are present in a reaction mixture at about the concentrations shown in Table 1.

29. The method of any of paragraphs 18-28, further comprising
performing PCR using known quantities of NRP-2 and Melan-A nucleic acids to generate a standard curve;
and calculating copy numbers of NRP-2 and Melan-A in the sample using the standard curve.

30. An assay for detecting a predisposition for a melanoma to become malignant, the assay comprising:
(a) measuring the level of neurophilin-2 (NRP-2) mRNA in a sample obtained from a subject with melanoma;
(b) measuring the level of Melan-A (MART) mRNA in the sample obtained from the subject; and
(c) calculating the value of NRP-2:MART from the levels obtained in steps (a) and (b);
wherein the melanoma is determined to have a predisposition to become malignant if the value of NRP-2:MART is increased relative to a reference level.

31. The assay of paragraph 30, wherein the sample is an FFPE sample.

32. The assay of any of paragraphs 30-31, wherein the levels of the mRNAs are measured using quantitative RT-PCR.

33. The assay of paragraph 32, wherein amplicons of less than 150 bp are amplified during PCR.

34. The assay of paragraph 32, wherein amplicons of less than 100 bp are amplified during PCR.

35. The assay of any of paragraphs 30-34, wherein a known quantity of an internal control nucleic acid is added to the sample prior to measuring the level of NRP-2 and Melan-A mRNAs.

36. The assay of any of paragraphs 30-35, wherein steps (a) and (b) comprise performing duplex RT-PCR wherein the level of the internal control nucleic acid is measured simultaneously with the measurement of NRP-2 and Melan-A mRNAs.

37. The assay of paragraph 36, wherein the level of NRP-2 or Melan-A is normalized to the level of the internal control nucleic acid prior to performing step (c).

38. The assay of any of paragraphs 30-37, wherein PCR is performed using one or more primers having the sequence of any of SEQ ID NOs: 1-2, 7-8, and 10-11.

39. The assay of any of paragraphs 30-38, wherein the level of amplicons resulting from PCR is detected using one or more probes having the sequence of any of SEQ ID NOs: 3, 9, and 12.

40. The assay of any of paragraphs 30-39, wherein the primers or probes are present in a reaction mixture at about the concentrations shown in Table 1.

41. The assay of any of paragraphs 30-40, further comprising
performing PCR using known quantities of NRP-2 and Melan-A nucleic acids to generate a standard curve;
and calculating copy numbers of NRP-2 and Melan-A in the sample using the standard curve.

42. The assay or method of any of paragraphs 1-41, wherein the assay or method further comprises measuring the level of one or more marker genes selected from the group consisting of:
IL8; AREG; MMP1; CSPG2; SerpinB2; RAP1A; FLRT3; CSPG2; COL4A1; TK1; DHFR; CDH3; HELLS; KIT; CXCL1; Ki67; MITF; p53; and p21;
wherein an increase in the marker gene relative to a reference level indicates malignant melanoma is detected in the sample or that the melanoma has a predisposition to become malignant.

43. A kit for performing the method or assay of any of paragraphs 1-42.

44. A method for treating a subject for melanoma, comprising administering a treatment for malignant melanoma to a subject that has been determined to have malignant melanoma.

45. The method of paragraph 44, where the subject was determined to have a malignant melanoma by an assay as paragraphed in paragraphs 1, 3-17, and 30-42.

46. The method of paragraphs 44 and 45, wherein the treatment comprises surgically removing the melanoma and administering adjuvant therapy and follow-up monitoring if the value of NRP-2:MART is increased at least 2 σ relative to a reference level; and not administering adjuvant therapy if the value of NRP-2:MART is not increased at least 2 σ relative to a reference level.

EXAMPLES

Example 1

Described herein is a diagnostic assay protocol utilizing duplex RT-PCR technique to quantitatively measure gene expression levels in melanoma tissue biopsies preserved in a form of formalin-fixed paraffin-embedded (FFPE). This diagnostic assay comprises two steps: step 1, quantitative measurement of gene transcript copy numbers by duplex RT-PCR and step 2, calculation of expression ratio of two genes (melanoma diagnostic biomarker gene, neurophilin-2 and melanocytic tumor reference gene, melan-A). This assay protocol generates numerical number of the gene expression ratio which is able to discriminate malignant melanomas from benign melanomas indicating this assay can be used as a diagnostic tool for malignant melanomas.

FFPE tissue represents the most common form of tissue sample archived throughout the clinics in worldwide. Therefore, FFPE tissue specimen is the most abundant supply of solid tissue specimens annotated with clinical outcome data. RNA extracted from FFPE tissue exists as fragments less than 300 bases in length (1,2). This presents a challenge for quantitative assessment gene expression. RT-PCR assay provides sensitive and quantitative means to measure gene expression levels in biopsies of patients. Quantitative RT- PCR assay of FFPE RNA can provide fast, large, and relatively inexpensive retrospective and prospective clinical studies to validate its potential in routine clinical diagnostic and prognostic assays.

Neuropilin-2 (NRP-2), a cell surface receptor involved in angiogenesis and axonal guidance, is a critical mediator of tumor-associated lymphangiogenesis (3). The inventors have demonstrated that NRP-2 is a novel biomarker for malignant melanoma as demonstrated in a panel of various tumor using immunohistochemical (IHC) analysis (4) which is a non-quantitative, time-consuming, and expensive assay method. Described herein is an assay protocol which utilizes duplex qRT-PCR technique. This assay method is convenient, quick, simple, and generates quantitative numerical values in contrast to IHC. This assay protocol has been validated using two independent sets of clinical samples of FFPE melanoma tissues. Critically, the expression ratios between the NRP2 and melan-A genes determined by the assay protocols described herein permit the user to distinguish malignant melanomas from benign. This result indicates that this assay is a useful diagnostic tool for melanomas.

REFERENCES

1. Rupp G M, Locker J. Purification and analysis of RNA from paraffin-embedded tissues. Biotechniques. 1988 January; 6(1):56-60.
2. Cronin M et al., Measurement of gene expression in archival paraffin-embedded tissues: development and performance of a 92-gene reverse transcriptase-polymerase chain reaction assay. Am J Pathol. 2004 January; 164(1): 35-42.
3. M. Caunt, J. Mak and W. C. Liang, et al. Blocking neuropilin-2 function inhibits tumor cell metastasis. Cancer Cell, 13 (2008), pp. 331-342.
4. Rushing E C et al. Neuropilin-2: a novel biomarker for malignant melanoma? Hum Pathol. 2011 Aug. 12. [Epub ahead of print]

Example 2: Exemplary Assay Protocol

Step 1
RNA Extraction from FFPE Tissue:

Two 10 μm sections of each FFPE tissue biopsy were used for RNA extraction. Total RNA was extracted from each tissue sample using Arcturus Paradise PLUS Whole Transcript Kit™ (Applied Biosystems, Foster City, Calif.) according to the manufacturer's instruction.

Addition of Internal Control Gene for Normalization:

RNA concentration was measured by nanodrop and 1 ug of total RNA was alquarted for reverse transcription. Luciferase mRNA (1.0 ng) purchased from Promega (Medison, Wis., USA) was ectopically added to the 1 ug of aliquarted RNA from each sample as an internal control for normalization of variations from subsequent steps of reverase transcription and PCR amplification.

Reverse Transcription:

Reverse transcription for synthesizing the first-strand cDNA was performed using a random-hexamer primer and SuperScript II reverse transcriptase (Invitrogen), according to the manufacturer's instructions, and used as a template for subsequent PCR amplification.

Standard curve generation for copy number calculation: 500 bp long cDNA fragments of neuropilin-2 and melan-A gene were PCR amplified from WM35 human melanoma cells by SYBR Green™ method. The amplifed DNA fragments were subjected to 2% agrose gel electroporesis and 500 bp DNA bands were excised and purified by using Qiaquick PCR Purification Kit™ (Qiagen). DNA content was measured by nanodrop and diluted to a concentration of 0.1 ng, 0.1 pg, and 0.1 fg per ul. The dilutions were used as a DNA template for Taqman™ PCR amplification. The corresponding Ct values and copy number of DNA fragments were used for standard curve generation. Primer sequences for the 500 bp cDNA template generation are: NRP2, forward 5'-GGATGCGGCTGGAGGTGCTG-3' (SEQ ID NO: 13) and reverse 5'-CCGCCCTGGTCCTCACGGAT-3' (SEQ ID NO: 14), melan-A, forward 5'-AGAACAGTCACCACCACCT-3' (SEQ ID NO: 15) and reverse 5'-GGCCAGTCAACCCTTTGTCTTAACC-3' (SEQ ID NO: 16).

Duplex Real-Time PCR Amplification:

Primer and probe sequences for duplex PCR. Primers were synthesized from Invitrogen. Primer sequences for duplex PC were intentionally designed to generate amplicons of each gene less than 100 bp because of the fragmentary nature of RNA extracted from FFPE tissues. Primer Taqman probe sequences for each genes, final concentration for duplex PCR, and amplicon sizes are shown in Table 1.

TABLE 1

Sequences of primers and probes, molar concentration, and amplicon sizes for each gene used in duplex RT-PCR.

| Genes | Sequences | Concentration (FM) | Amplicon sizes (bp) | SEQ ID NO |
|---|---|---|---|---|
| NRP2 | 5'-gactccaagcccacggtaga-3' (F) | 0.3 | 58 | 1 |
|  | 5'-tggttgtctcttcgctcttcac-3' (R) | 0.3 |  | 2 |
|  | 6FAM-acgctgggacccac-MGBNFQ (P) | 12.5 |  | 3 |
| ACTB | 5'-ccagctcaccatggatgatg-3' (F) | 1.2 | 57 | 4 |
|  | 5'-atgccggagccgttgtc-3' (R) | 1.2 |  | 5 |
|  | 6FAM-tatcgccgcgctcg-MGBNFQ (P) | 6.25 |  | 6 |
| Melan-A | 5'-gggccatccaatttctctttactt-3' (F) | 0.9 | 74 | 7 |
|  | 5'-atgtcggtcaaggttcgaaaa-3' (R) | 0.9 |  | 8 |
|  | 6FAM-ttggctaataacaaactagtca-MGBNFQ (P) | 6.25 |  | 9 |

TABLE 1-continued

Sequences of primers and probes, molar concentration, and amplicon sizes for each gene used in duplex RT-PCR.

| Genes | Sequences | Concentration (FM) | Amplicon sizes (bp) | SEQ ID NO |
|---|---|---|---|---|
| Luciferase | 5'-cgatgacgccggtgaac-3' (F) | 0.3 | 55 | 10 |
| | 5'-cgtctttccgtgctccaaaa-3' (R) | 0.3 | | 11 |
| | VIC-tcccgccgccgtt-MGBNFQ (P) | 6.25 | | 12 |

F = forward primer, R = reverse primer, P = TaqMan probe

Duplex PCR Mix and Amplification Condition.

PCR Amplification was performed using a StepOnePlus™ Real-Time PCR System (Applied Biosystems, Foster City, Calif.). Reaction mixtures for each gene were:

NRP2:

| 2X Taqman master mix | 10.0 ul |
|---|---|
| Primer mix for NRP2 (10 uM) | 0.6 ul |
| Primer mix for Luciferase (10 uM) | 0.6 ul |
| Probe for NRP2 (10 uM) | 0.25 ul |
| Probe for Luciferase | 0.25 ul |
| Sample | 1.0 ul |
| Nuclease free ddH2O | 7.3 ul |
| Total | 20.0 ul |

Melan-A:

| 2X Taqman master mix | 10.0 ul |
|---|---|
| Primer mix for ACTB (10 uM) | 1.8 ul |
| Primer mix for Luciferase (10 uM) | 0.6 ul |
| Probe for NRP2 (10 uM) | 0.12 ul |
| Probe for Luciferase | 0.12 ul |
| Sample | 1.0 ul |
| Nuclease free ddH2O | 6.36 ul |
| Total | 20.0 ul |

The Amplification Cycling Conditions.

A two-step amplification cycling method was used. Initial holding stage: 50° C. 2:00 min and 95° C. 10:00 min (1 cycle) Cycling stage: 95° C. 15 sec. and 60° C. 60 sec. (60 cycles).

Step 2

Calculation of Gene Expression Ratio (Data Analysis).

The average of Ct values of luciferase mRNA (internal control) spiked in the samples was obtained. The normalization factor for each sample was calculated (Ct values of each sample's luciferase gene divided by average Ct value of luciferase of all samples). These normalization factors were used for the calculation of corrected Ct values of NRP2 and melan-A genes. These normalization steps were necessary to correct sample variations which were introduced in the reverse transcription and PCR amplifications steps. The corrected Ct values of each gene from each sample were used to calculate each gene transcript copy numbers using standard curves. In order to compensate for the differences of melanocytic tumor size of each tissue samples, the expression ratio of NRP2 gene was calculated by dividing by melanocytic tumor marker gene (melan-A) copy numbers. This numerical value (ratio of NRP2 and melan-A gene copy numbers) was proven to be a useful indicator for distinguishing malignant melanomas from benign melanocytic lesions.

The accuracy of the assay protocol described above was evaluated in two independent sets of clinical melanoma samples. The resulting data strongly indicate the utility of this assay as a melanoma diagnostic tool.

These primers described herein were designed to produce a short PCR amplicon since the RNA extracted from FFPE tissue samples exists as short and fragmented forms. The successful amplification of the NRP-2 gene transcript using this qRT-PCR amplification conditions permit the measurement of the expression levels of target gene quantitatively in FFPE tissue samples. This technique can be used for the assessment of other genes of interest which are associated with biological processes of melanomagenesis and progression. Therefore, it is possible to do multigene-expression assay from FFPE tissue samples. The use of melanocytic tumor reference gene, melan-A, for the compensation of tumor size differences of each biopsy is demonstrated herein to eliminate tumor microdisection step and simplify the assay process. The assay described herein can also be performed using other types of samples such as, e.g., blood, saliva, and other bodily fluids.

The assay described herein, or a kit comprising reagents for performing the assay described herein can permit the diagnosis and prognose malignant melanoma. These qRT-PCR assays are quantitative, fast, and simple compared to IHC and thereby provide more sensitive and accurate diagnostic information.

Example 3: A Potential Biomarker Neuropilin-2 Gene Expression Correlates with Malignant Progression in Cutaneous Melanomas Predicting the aggressiveness of early melanoma lesions by histological examination is challenging. Molecular biomarkers that could identify high-risk melanoma patients as early as possible would contribute to increased survival. Neuropilin-2 (NRP2), a cell surface receptor involved in tumor-associated angiogenesis and lymphangiogenesis, is highly expressed in malignant melanomas.

Described herein is the demonstration of assays relating to the use of NRP2 gene transcript as a prognostic biomarker for malignant progression.

NRP2 gene expression was measured in a panel of formalin-fixed paraffin-embedded (FFPE) tissue specimens consisted of nevi, primary melanomas, and metastatic melanomas using quantitative reverse transcriptase polymerase chain reaction technique. It is demonstrated herein that NRP2 levels are clearly segregated among the sample groups of nevi, primary melanomas, and metastatic melanomas with a trend of increasing NRP2 expression correlating with disease progression. There is a positive correlation (r=0.823) between NRP2 expression and Breslow depth in primary melanomas. Logistic regression analysis shows that the probability of malignant progression increased with elevated levels of NRP2 (odds ratio of 2.60 with CI 1.29-5.21). This result indicates that NRP2 levels, measured in accordance with the assays described herein, is a useful prognosticator for early identification of high-risk melanoma patients.

Within the group of primary melanomas, there is a positive correlation (r=0.823) between NRP2 expression and Breslow depth. This correlation was validated in an independent sample set of patients with melanoma. The data presented herein demonstrates that NRP2 is a useful biomarker for malignant progression of melanoma, which may be useful for early identification of patients with melanoma at high risk.

Introduction.

The high mortality rate of advanced melanoma presents a significant clinical challenge due to inadequate treatment strategies [1]. To date, early diagnosis followed by appropriate complete surgical excision is the mainstay of treatment in affected individuals. In addition to the refractory nature of malignant melanomas to current treatment options, an additional compounding issue is the lack of accurate biomarkers for identification of high-risk patients [2, 3]. Thus, there is a critical need for biomarkers to early identify high-risk patients and to guide treatment decisions [4].

Neuropilins, transmembrane glycoproteins, are crucial in neural and vascular development and are receptors for two different ligand families: the semaphorin family, which is involved in axonal guidance and VEGF family members, which mediate angiogenesis [5, 6]. While Neuropilin-1 is expressed in epithelial cells, Neuropilin-2 (NRP2) expression is predominant in venous and lymphatic endothelial cells and tumors of neural crest origin, such as melanoma, glioblastoma, and neuroblastoma [7]. In melanoma, cell-to-cell communication between tumor cells and endothelial cells stimulates expression of NRP2, which plays a critical role in tumor cell growth and survival [8]. Furthermore, increased expression of NRP2 protein levels is found in melanoma compared to normal tissues using immunohistochemical analysis [9]. Described herein is the evaluation of the prognostic relevance of quantitative NRP2 gene expression using reverse transcription polymerase chain reaction (RT-PCR) on formalin-fixed paraffin-embedded (FFPE) archival material of melanoma tissue samples.

Materials and Methods

Patients and Tissue Samples:

This study was approved by the Institutional Review Board of Boston University School of Medicine. Archival materials between 2009-2011 with a diagnosis of malignant melanoma were retrieved from the pathology files of Skin Pathology Laboratory, Boston University School of Medicine, Boston, Mass. A total of 33 formalin-fixed paraffin-embedded cases (9 primary, 12 metastatic melanomas, and 12 nevi) were identified as meeting the criteria for inclusion in the study, based on histopathologic diagnosis per Snomed codes and availability of sufficient tissue for PCR analyses. Clinical and histopathologic information including prognostication details of cases of primary cutaneous melanoma, as well as age, gender, and site of tissue sample for the patients with metastases and nevi, are shown in FIG. 3. The primary melanomas had a median depth of 1.38 mm (range 0.45 mm-1.65 mm) and three of these samples possess ulceration.

RNA Extraction and Reverse Transcription:

Two 10 μm sections of each FFPE tissues were used for total RNA extraction and reverse transcription. Luciferase mRNA (10 ng) purchased from Promega (Medison, Wis., USA) was ectopically added to each sample as an internal control. Total RNA was isolated from each tissue sample and treated with DNase using Arcturus Paradise PLUS Whole Transcript™ Kit (Applied Biosystems, Foster City, Calif.) according to the manufacturer's instruction. Reverse transcription was performed using SuperScript III™ First-Strand Synthesis System (Invitrogen, Carlsbad, Calif.) with random hexamers according to protocols provided by the manufacturer.

Duplex Quantitative Real-Time PCR:

Primers and TaqMan MGB Probes for corresponding genes were designed using the mRNA sequences as found in the NCBI's reference sequence database (available on the World Wide Web at ncbi.nlm.nih.gov/refseq/) using an online primer design software known as Primer-BLAST™ (available on the World Wide Web at ncbi.nlm.nih.gov/tools/primer-blast/) and Primer Expression Software 3.0™ (Applied Biosystem, Foster City, Calif.), respectively. Sequences of the primer sets and TaqMan probes for duplex quantitative real-time PCR of each target gene are shown in Table 1. Two different types of fluorescent dye labeled probes were utilized for the duplex quantitative real-time PCR assay, which allows detection and quantification of two gene transcripts (target and reference genes simultaneously) in a single reaction mixture. PCR amplifications were performed using a StepOnePlus Real-Time PCR™ System (Applied Biosystems, Foster City, Calif.) in a reaction volume of 20 μl containing 1×TaqMan Universal PCR Master Mix II, 1 μl of template cDNA, paired primers and TaqMan MGB probes for targeting gene of interest and exogenously added Luciferase RNA, which served as a loading control. Primers and probe concentrations for each target gene were synthesized from Applied Biosystems Inc. (ABI) and pre-optimized for duplex PCR reactions (Table 1). The PCR amplifications were initiated with an initial denaturing step at 95° C. for 5 min, followed by 60 cycles of simultaneous annealing and extension at 60° C. for 1 minute, followed by denaturation at 95° C. for 15 seconds (two-step amplification). Each reaction was run in duplicate. To quantitatively measure the target gene expression levels (NRP2 and ACTB), the ectopically spiked control gene (Luciferase) and a reference gene (Melan-A) were also PCR amplified. The ratio of the target gene and Luciferase was calculated to normalized steps for RNA extraction, reverse transcription, and PCR amplification. Melan-A was used to normalize for the size difference of melanocytic lesions of each tissue sample.

Standard Curves:

To generate the standard curves, a quantification protocol for real-time PCR provided by ABI was modified (Absolute Quantification Getting Started Guide, ABI, Foster City, Calif.). In brief, about 500 bp DNA fragments harboring target gene amplicons were PCR amplified from WM35 melanoma cells. The DNA fragments were separated by 2% agarose gel electrophoresis and purified using QIAquick® Gel Extraction Kit (Qiagen, Germantown, Md.). DNA concentrations were determined with NanoDrop 2000™ Spectrophotometer (Thermo Scientific, Waltham, Mass.). Copy numbers were calculated using the following formula: m=[n][1.096e-21 g/bp], where: n=plasmid size (bp), m=mass. The mass of DNA fragment needed for a given copy number was obtained by multiplying the mass of the 500 bp PCR amplified DNA with the copy number of interest. The prepared standard solutions were distributed into small aliquots and stored at −20° C. and thawed only once before use. The standard curves for each gene of interest were obtained using the 500 bp DNA fragment containing target genes ranging from 30 to 300,000 copies with primers and probes in duplex with Luciferase for internal control. The curves generated for each gene of interest showed a linear relationship between copy numbers and the CT values of real-time PCR for both target genes and Luciferase gene.

Statistical Analysis:

Logistic regression analysis was conducted to model the odds ratio of metastatic melanomas versus nevi cases or primary melanoma diagnoses as a function of NRP2 and ACTB. Analysis of variance techniques were used to analyze the biomarkers (NRP2 and ACTB) values by type of sample (nevi, primary melanoma, or metastatic melanoma). Comparison among the sample types was tested using the Tukey-Kramer test to adjust for multiple comparisons.

Results

An exploratory study was conducted to evaluate the prognostic significance of NRP2 gene expression in archival FFPE melanoma tissue samples. NRP2 transcript levels were compared in three groups of FFPE tissue samples of nevi, primary cutaneous melanomas, and metastatic melanomas, respectively. Since others reported that long-term stored FFPE extracts displayed degraded RNA ranging from 50 to 150 bp [10], primers were designed to limit the PCR amplicon length to less than 100 bp (58 bp for NRP2, 57 bp for ACTB, 74 bp for Melan-A, and 55 bp for Luciferase) (Table 1). Duplex qRT-PCR analysis of NRP2 expression was successfully performed in a panel of FFPE samples (nevi, n=12; primary, n=9; metastases, n=12) as described in the experimental method. FIG. 1A shows distinctive differences in NRP2 gene expression levels among the three groups; NRP2 expression levels increase in order from nevi, primary melanomas, to metastases. Statistical evaluation using analysis of variance (ANOVA) techniques demonstrates that the differences among sample groups were significant in NRP2 ($p<0.001$) but not in control gene beta-actin (ACTB) ($p=0.106$) (FIG. 1B). Intergroup comparison analysis of NRP2 gene expression by Tukey-Kramer test for multiple comparisons shows significant differences for primary vs. metastasis ($p=0.013$), and nevi vs. metastasis ($p<0.001$), but not for nevi vs. primary ($p=0.538$) (FIG. 1A). Furthermore, NRP2 expression levels in primary melanomas appear to correlate with Breslow depth (correlation coefficient, 0.823) (FIG. 1C). This indicates that NRP2 is a prognostic biomarker.

To calculate the predictive value of NRP2 expression levels for malignant progression, a logistic regression analysis was performed. The probability of malignant progression increased with increasing expression levels of NRP2 but not ACTB. The odds ratio for metastatic disease associated with an increase in NRP2 equal to one relative standard deviation was 2.60 (95% CI 1.29-5.21, Table 2). These findings therefore indicate that quantitative measurement of NRP2 gene expression is a prognostic indicator for high-risk melanoma patient identification.

Figure 6A:
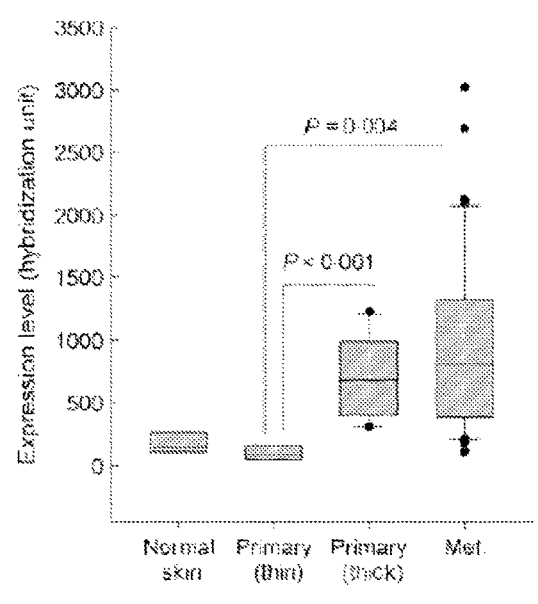
FIGS. 6A-6B demonstrate that NRP2 gene expression patterns and correlations with Breslow thickness in a microarray gene expression profile dataset of cryopreserved tissue specimens obtained from patients with melanoma. Box plots of NRP2 gene expression levels in sample groups of normal skin (n=4), thin primary melanomas (Breslow depth of <1.5 mm, n=6), thick primary melanomas (Breslow depth of >3.5, n=10) and metastatic melanomas (Met.) [22 bulky, macroscopic (replaced) lymph node metastases, 16 subcutaneous and two distant metastases of adrenal and brain, n=40]
Figure 6B:
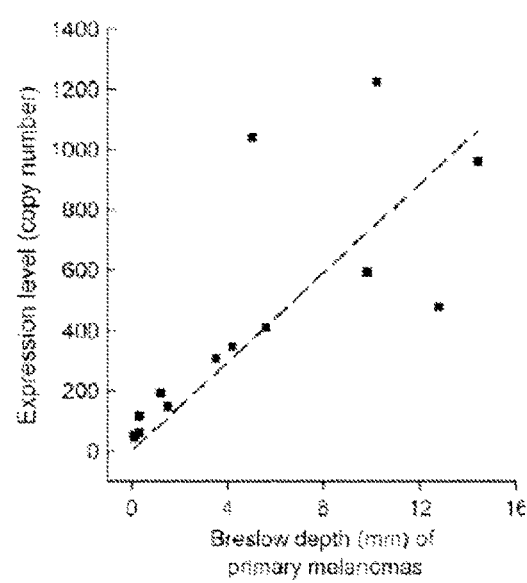

NRP2 gene expression patterns were further analyzed in a microarray data-set of gene expression profile of tissue samples cryopreserved in liquid nitrogen from a different cohort of melanoma patients. 11 In this additional analysis, very similar patterns of NRP2 gene expression were noted between the two independent groups of patients (FIG. 6A). The NRP2 gene expression increased dramatically in thick primary melanomas (>3.5 mm, n=10) and metastases (n=40) compared with thin primary melanomas (<1.5 mm, n=6) and normal skin (n=4). NRP2 expressions in primary melanomas were found to strongly correlate with the Breslow thickness (n=14, primary melanomas with Breslow depth of <14.4 mm including two melanoma in situ, correlation coefficient=0.763 with P-value=0.002) (FIG. 6B). These results indicate that quantitative measurement of NRP2 gene expression is a molecular indicator for malignant progression of early melanoma and can permit identification of patients with melanoma at high risk.

Discussion

Described herein is a reliable and quantitative assay technique that can be used for NRP2 biomarker assessment in melanoma using FFPE archival tissues samples. In order to quantitatively assess NRP2 expression in the FFPE tissue specimens, the copy numbers of the target gene (NRP2) were normalized by a reference gene (Melan-A) for the comparison of the gene expression levels of each transcript in the tissue samples analyzed. Melan-A was chosen as a reference gene since it has been reported that its expression levels show no significant changes as melanocytic lesions progress to malignant melanomas, contrary to other melanocytic markers such as c-Kit, MITF, and HMB-45, [14]. Additionally, Nielsen et al. also reported that quantification of Ki67 expression normalized by melan-A expression served better as a marker for discrimination of melanoma from nevi than Ki67 alone [15]. These studies suggest that melan-A is a useful reference gene for quantitative assays of gene expression in melanocytic tumors. Implementation of this normalization step provides a convenient compensation method for the size differences of melanocytic lesions in each tissue sample; therefore, greatly simplifying the assay protocol without compromising accuracy of assay results. This assay method also generates quantifiable and objective values of results for easier interpretation compared to the immunohistochemical assay.

While early stage melanomas (AJCC Stage I and II) may progress to advanced disease, there is currently no standardized adjuvant therapy regiment recommended for such patients due to a lack of clear clinical benefits for this large cohort of patients. Consequently, early stage melanoma patients are typically treated with surgical excision alone [16]. Identification of a subset of high-risk individuals among early stage melanoma patients at the time of initial diagnosis and surgical treatment is needed as early selective treatment with adjuvant therapy by physicians may increase survival benefits for patients with high-risk of metastatic recurrence. Thus, the development of reliable prognostic assay tools for melanoma is in high demand [17, 18].

Clinically well established melanoma prognostic indicators such as tumor thickness, ulceration, and mitotic activity likely represent surrogates of key biological events that occur during the course of malignant progression [19]. Understanding the correlations between these established prognostic factors and the underlying molecular events which drive disease progression may yield additional key molecular markers and therapeutic targets. In addition, molecules that are key players in functional pathways related to aggressive phenotypes may produce melanoma prognostic markers which are independent of the existing clinicopathologic features (reviewed in [17, 18]). Such phenotypes of malignant tumor include tissue invasion and metastasis, self-sufficiency in growth signals, resistance to apoptosis, and altered immune-competence. Sustained tumor angiogenesis is also an important aggressive phenotype.

Molecules regulating the tumor-specific angiogenesis pathway may be excellent candidates for prognostic indicator for melanoma. Tumor-specific angiogenesis and lymphangiogenesis facilitate malignant progression and metastasis, which are driven by a host of different growth factors, including vascular endothelial growth factors (VEGFs) [20]. NRP2 is a co-receptor that enhances responses to many growth factors including VEGFs. NRP2 is expressed in venous cells and malignant tumor cells. Inhibition of NRP2 showed a suppressive effect on metastasis in pre-clinical models [7, 29].

Described herein are experiments demonstrating that NRP2 expression levels significantly differ between primary and metastatic melanomas using a novel quantitative assay protocol with FFPE specimens (FIG. 1A). Furthermore, even though small number of patient samples with high degree of gender bias (8 of 9 samples were from male patients) was used in this study, NRP2 mRNA expression levels are closely correlated with tumor thickness in the early stages of primary melanomas (FIG. 1C). Without wishing to be bound by theory, this suggests that there is a trend of higher NRP2 gene expression in thicker melanoma lesions. This trend indicates that NRP2 can be used as a companion prognostic biomarker with the Bleslow depth, which is one of the most important macroscopic prognostic indicators for malignant melanoma.

Three VEGF isoforms (VEGF-A, VEGF-C and VEGF-B) and all VEGF receptors were studied to evaluate potential value as prognostic indicators in melanoma using clinical samples. However, only the VEGF-receptor-3 (FLT-4) is positively related between primary and metastatic melanoma[21] and none showed a significant trend related to Breslow depth.[17,18]

As described herein, NRP2 gene expression levels differed significantly between early stage primary melanoma and metastatic melanoma, using a novel quantitative assay protocol with FFPE specimens (FIG. 1A). The data further indicate that there is a trend of higher NRP2 gene expression in thicker melanoma lesions. The positive correlation between NRP2 gene expression and tumour thickness in primary melanoma was validated with a large, independent dataset of gene expression profiles for melanoma (FIG. 6B). Accordingly, it is contemplated herein that NRP2 expression levels can be used in combination with Breslow depth in the aspects and embodiments described herein.

It is demonstrated herein that NRP2 expression as a quantifiable prognostic indicator which permits the identification of patients who have a high-risk of metastatic recurrence.

REFERENCES

[1] Balch C M, Gershenwald J E, Soong S J, Thompson J F, Atkins M B, Byrd D R, et al. Final version of 2009 AJCC melanoma staging and classification. J Clin Oncol. 2009 Dec. 20; 27(36):6199-206.

[2] Bhatia S, Tykodi S S, Thompson J A. Treatment of metastatic melanoma: an overview. Oncology (Williston Park, N Y. 2009 May; 23(6):488-96.

[3] Nashan D, Muller M L, Grabbe S, Wustlich S, Enk A. Systemic therapy of disseminated malignant melanoma: an evidence-based overview of the state-of-the-art in daily routine. J Eur Acad Dermatol Venereol. 2007 November; 21(10):1305-18.

[4] Nathanson K L. Using genetics and genomics strategies to personalize therapy for cancer: focus on melanoma. Biochemical pharmacology. 2010 Sep. 1; 80(5):755-61.

[5] Klagsbrun M, Takashima S, Mamluk R. The role of neuropilin in vascular and tumor biology. Advances in experimental medicine and biology. 2002; 515:33-48.

[6] Kolodkin A L, Levengood D V, Rowe E G, Tai Y T, Giger R J, Ginty D D. Neuropilin is a semaphorin III receptor. Cell. 1997 Aug. 22; 90(4):753-62.

[7] Bielenberg D R, Pettaway C A, Takashima S, Klagsbrun M. Neuropilins in neoplasms: expression, regulation, and function. Experimental cell research. 2006 Mar. 10; 312 (5):584-93.

[8] Stine M J, Wang C J, Moriarty W F, Ryu B, Cheong R, Westra W H, et al. Integration of genotypic and phenotypic screening reveals molecular mediators of melanoma-stromal interaction. Cancer research. 2011 Apr. 1; 71(7):2433-44.

[9] Rushing E C, Stine M J, Hahn S J, Shea S, Eller M S, Naif A, et al. Neuropilin-2: a novel biomarker for malignant melanoma? Human pathology. 2012 March; 43(3): 381-9.

[10] Cronin M, Pho M, Dutta D, Stephans J C, Shak S, Kiefer M C, et al. Measurement of gene expression in archival paraffin-embedded tissues: development and performance of a 92-gene reverse transcriptase-polymerase chain reaction assay. The American journal of pathology. 2004 January; 164(1):35-42.

[11] Linton K M, Hey Y, Saunders E, Jeziorska M, Denton J, Wilson C L, et al. Acquisition of biologically relevant gene expression data by Affymetrix microarray analysis of archival formalin-fixed paraffin-embedded tumours. British journal of cancer. 2008 Apr. 22; 98(8):1403-14.

[12] Paik S, Shak S, Tang G, Kim C, Baker J, Cronin M, et al. A multigene assay to predict recurrence of tamoxifen-treated, node-negative breast cancer. The New England journal of medicine. 2004 Dec. 30; 351(27):2817-26.

[13] Lebbe C, Guedj M, Basset-Seguin N, Podgorniak M P, Menashi S, Janin A, et al. A reliable method for the selection of exploitable melanoma archival paraffin embedded tissues for transcript biomarker profiling. PloS one. 2012; 7 (1):e29143.

[14] Nazarian R M, Prieto V G, Elder D E, Duncan L M. Melanoma biomarker expression in melanocytic tumor progression: a tissue microarray study. Journal of cutaneous pathology. April; 37 Suppl 1:41-7.

[15] Nielsen P S, Riber-Hansen R, Raundahl J, Steiniche T. Automated quantification of MART 1-verified Ki67 indices by digital image analysis in melanocytic lesions. Archives of pathology & laboratory medicine. June; 136 (6):627-34.

[16] Tsao H, Atkins M B, Sober A J. Management of cutaneous melanoma. The New England journal of medicine. 2004 Sep. 2; 351(10):998-1012.

[17] Gould Rothberg B E, Rimm D L. Biomarkers: the useful and the not so useful—an assessment of molecular prognostic markers for cutaneous melanoma. The Journal of investigative dermatology. August; 130(8): 1971-87.

[18] Tanaka R, Koyanagi K, Narita N, Kuo C, Hoon D S. Prognostic molecular biomarkers for cutaneous malignant melanoma. Journal of surgical oncology. September; 104 (4):438-46.

[19] Spatz A, Batist G, Eggermont A M. The biology behind prognostic factors of cutaneous melanoma. Current opinion in oncology. May; 22(3):163-8.

[20] Mahabeleshwar G H, Byzova T V. Angiogenesis in melanoma. Seminars in oncology. 2007 December; 34(6): 555-65.

[21] Brychtova S, Bezdekova M, Brychta T, Tichy M. The role of vascular endothelial growth factors and their receptors in malignant melanomas. Neoplasma. 2008; 55(4):273-9.

[22] Depasquale I, Thompson W D. Prognosis in human melanoma: PAR-1 expression is superior to other coagulation components and VEGF. Histopathology. 2008 March; 52(4):500-9.

[23] Emmett M S, Dewing D, Pritchard-Jones R O. Angiogenesis and melanoma—from basic science to clinical trials. American journal of cancer research. 2011; 1(7): 852-68.
[24] Erhard H, Rietveld F J, van Altena M C, Brocker E B, Ruiter D J, de Waal R M. Transition of horizontal to vertical growth phase melanoma is accompanied by induction of vascular endothelial growth factor expression and angiogenesis. Melanoma research. 1997 August; 7 Suppl 2:S19-26.
[25] Marcoval J, Moreno A, Graells J, Vidal A, Escriba J M, Garcia-Ramirez M, et al. Angiogenesis and malignant melanoma. Angiogenesis is related to the development of vertical (tumorigenic) growth phase. Journal of cutaneous pathology. 1997 April; 24(4):212-8.
[26] Mouawad R, Spano J P, Comperat E, Capron F, Khayat D. Tumoural expression and circulating level of VEGFR-3 (Flt-4) in metastatic melanoma patients: correlation with clinical parameters and outcome. Eur J Cancer. 2009 May; 45(8):1407-14.
[27] Salven P, Heikkila P, Joensuu H. Enhanced expression of vascular endothelial growth factor in metastatic melanoma. British journal of cancer. 1997; 76(7):930-4.
[28] Straume O, Akslen L A. Importance of vascular phenotype by basic fibroblast growth factor, and influence of the angiogenic factors basic fibroblast growth factor/fibroblast growth factor receptor-1 and ephrin-A1/EphA2 on melanoma progression. The American journal of pathology. 2002 March; 160(3):1009-19.
[29] Jubb A M, Sa S M, Ratti N, Strickland L A, Schmidt M, Callahan C A, et al. Neuropilin-2 expression in cancer. Histopathology. September; 61(3):340-9. [30] Wititsuwannakul J, Mason A R, Klump V R, Lazova R. Neuropilin-2 as a useful marker in the differentiation between Spitzoid malignant melanoma and Spitz nevus. Journal of the American Academy of Dermatology. January; 68(1): 129-37.

TABLE 2

Logistic regression analysis predicting probability of malignant progression as a function of NRP2 and ACTB gene expression (odds ratios associated with an increase in one relative standard deviation in the analyte).

| Statistics | Biomarkers (analytes) | |
| --- | --- | --- |
| | NRP2 | ACTB |
| Logistic Regression P-value | 0.007 | 0.236 |
| Odd Ratio (95% CI) | 2.60 (1.29, 5.21) | 1.02 (0.99, 1.04) |

Example 4

Figure 4A:
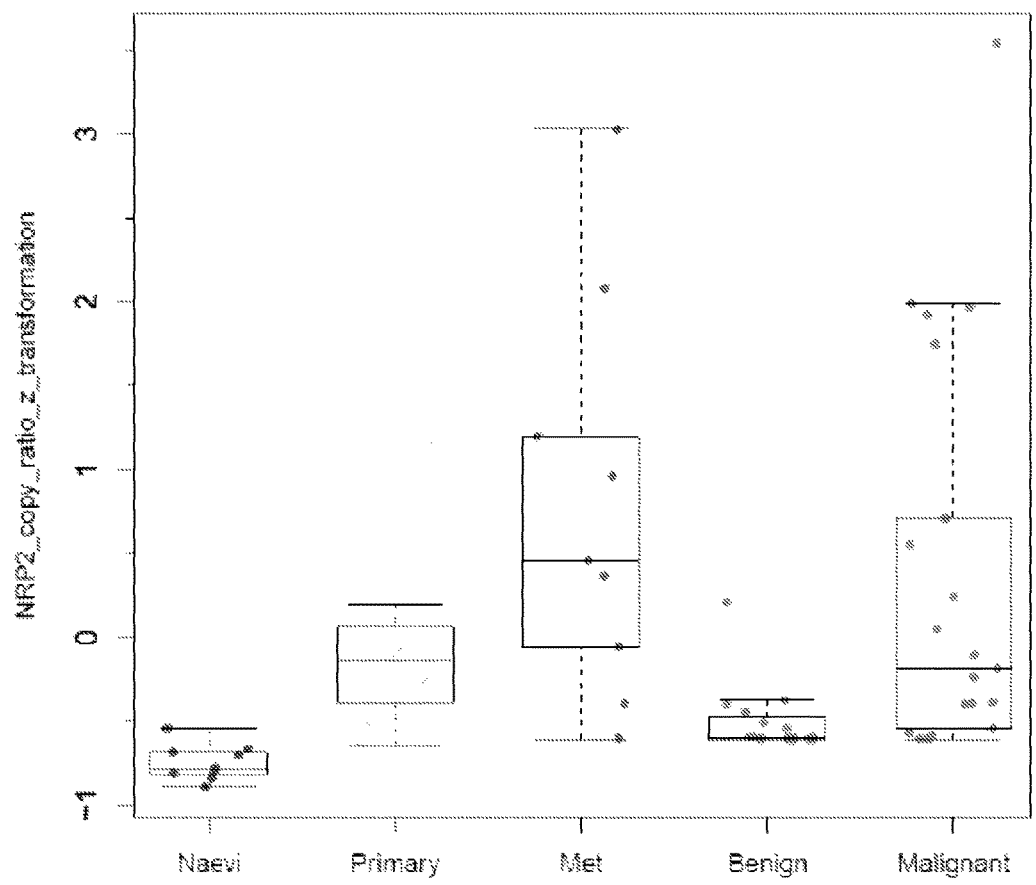
FIGS. 4A-4B demonstrate NRP2 expression (copy ratio of NRP2 to Melan-A) in different groups of clinical tissue specimens after z score transformation.
Figure 4B:
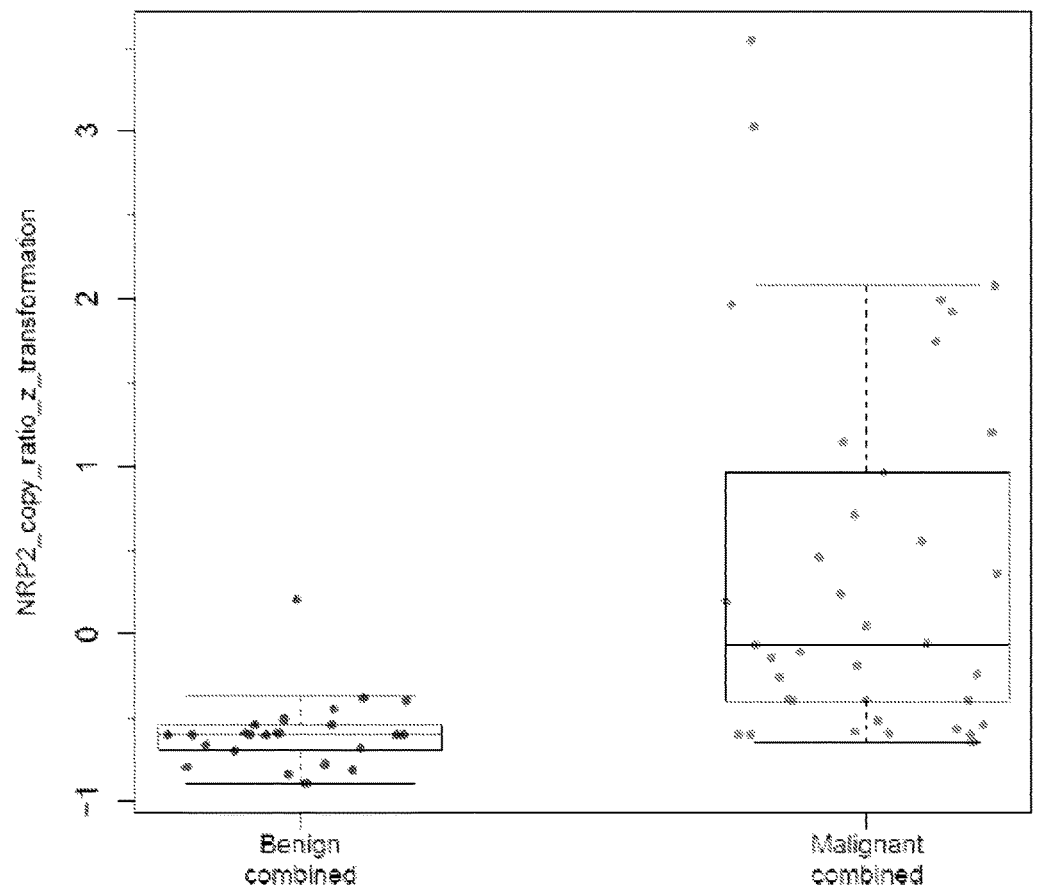
Figure 5:
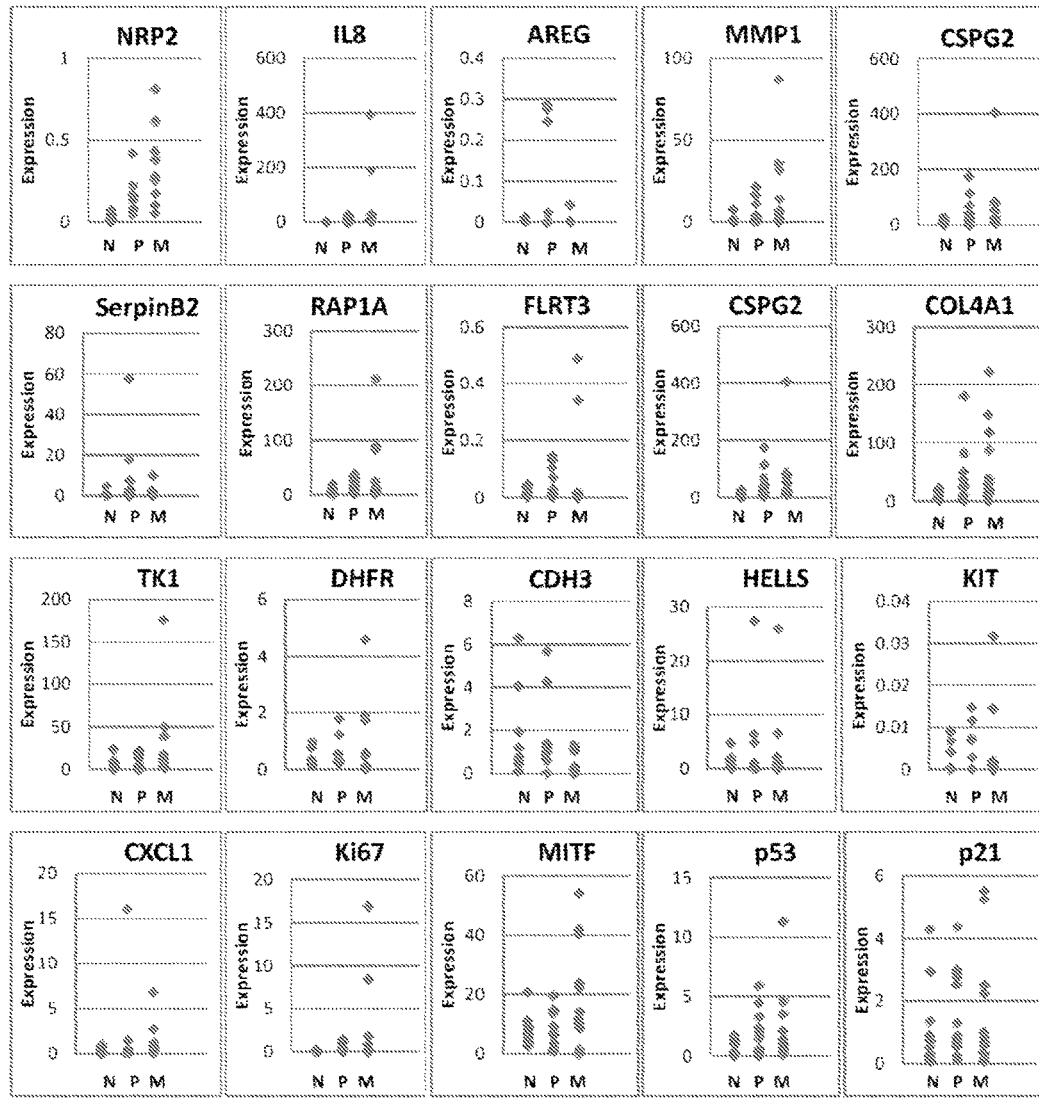
FIG. 5 demonstrates quantitative measurement of multiple gene expression levels in the three groups of patient tissue samples (N: nevi, n=12; P: primary melanomas, n-12; M: metastatic melanomas, n=12). Expression levels of each gene calculated by the ratio of gene transcript copy numbers between target gene and Melan-A.

NRP2 expression (copy ratio of NRP2 to Melan-A) was determined in different groups of clinical tissue specimens after z score transformation (FIG. 4A-4B). Quantitative measurement of multiple gene expression levels in the three groups of patient tissue samples was also performed. Expression levels of each gene were calculated by the ratio of gene transcript copy numbers between target gene and Melan-A. Candidate genes were selected form gene expression signatures associated with malignant melanoma progression. Some genes with roles in tumor suppression (p53 and 021), proliferation (Ki67), and melanocyte differentiation (MITF) were included. The same assay protocol as for the NRP2 such as RNA extraction, reverse transcription, PCR amplification, and normalization was used except primers and probe sequences which are unique for each target gene. This multigene assay result demonstrates that the assay protocol for the quantitative measurement of NRP2 can be applied for multigene assay as a melanoma biomarker (FIG. 5).

What is claimed herein is:

1. A method of treatment for melanoma, the method comprising:
   (a) performing quantitative duplex RT-PCR on a sample obtained from a subject to measure:
      (1) the level of neurophilin-2 (NRP-2) in the sample; and
      (2) a known quantity of an internal control nucleic acid added to the sample; and normalizing the level of NRP-2 to the level of the internal control nucleic acid;
   (b) performing quantitative duplex RT-PCR on a sample obtained from the subject to measure:
      (1) the level of melan-A (MART) in the sample; and
      (2) a known quantity of an internal control nucleic acid added to the sample; and normalizing the level of MART to the level of the internal control nucleic acid;
   (c) calculating the value of NRP-2:MART from the levels obtained in steps (a) and (b); and
   (d) (i) surgically removing the melanoma and administering adjuvant therapy and follow-up monitoring if the value of NRP-2: MART is increased at least 2 σ relative to a reference level; and
      (ii) surgically removing the melanoma and not administering adjuvant therapy if the value of NRP-2: MART is not increased at least 2 σ relative to a reference level.

2. The method of claim 1, wherein PCR is performed using one or more primers having the sequence of any of SEQ ID NOs: 1-2, 7-8, or 10-11.

3. The method of claim 2, wherein the primers of SEQ ID NOs: 1-2 are present in a reaction mixture at about 0.3 FM, the primers of SEQ ID NO:s 7-8 are present in a reaction mixture at about 0.9 FM, or the primers of SEQ ID NOs: 10-11 are present in a reaction mixture at about 0.3 FM.

4. The method of claim 1, wherein the level of amplicons resulting from PCR is detected using one or more probes having the sequence of any of SEQ ID NOs: 3, 9, or 12.

5. A method of treatment for melanoma, the method comprising:
   (a) measuring the level of neurophilin-2 (NRP-2) mRNA in a sample obtained from a subject with melanoma;
   (b) measuring the level of melan-A (MART) mRNA in the sample obtained from the subject;
   (c) calculating the value of NRP-2:MART from the levels obtained in steps (a) and (b); and
   (d) (i) surgically removing the melanoma and administering adjuvant therapy and follow-up monitoring if the value of NRP-2:MART is increased relative to a reference level; and
      (ii) surgically removing the melanoma and not administering adjuvant therapy if the value of NRP-2: MART is not increased relative to a reference level.

6. The method of claim 5, wherein the sample is an FFPE sample.

7. The method of claim 5, wherein the levels of the mRNAs are measured using quantitative RT-PCR.

8. The method of claim 7, wherein the amplicon products amplified during PCR are of less than 150 bp in length.

9. The method of claim 7, wherein the amplicon products amplified during PCR are of less than 100 bp in length.

10. The method of claim 5, wherein a known quantity of an internal control nucleic acid is added to the sample prior to measuring the level of NRP-2 and Melan-A mRNAs.

11. The method of claim 5, wherein steps (a) and (b) comprise performing duplex RT-PCR wherein the mRNA level of the internal control nucleic acid is measured simultaneously with the measurement of NRP-2 and Melan-A mRNAs.

12. The method of claim 11, wherein the mRNA level of NRP-2 or Melan-A is normalized to the level of the internal control nucleic acid prior to performing step (c).

13. The method of claim 5, wherein one or both of the measuring steps comprises performing PCR using one or more primers having the sequence of any of SEQ ID NOs: 1-2, 7-8, and 10-11.

14. The method of claim 13, wherein the level of amplicons resulting from PCR is detected using one or more probes having the sequence of any of SEQ ID NOs: 3, 9, and 12.

15. The method of claim 13, wherein the primers of SEQ ID NOs: 1-2 are present in a reaction mixture at about 0.3 FM, the primers of SEQ ID NO:s 7-8 are present in a reaction mixture at about 0.9 FM, or the primers of SEQ ID NOs: 10-11 are present in a reaction mixture at about 0.3 FM.

16. The method of claim 5, further comprising measuring the mRNA level of one or more marker genes selected from the group consisting of:
   IL8, AREG, MMP1, CSPG2, SerpinB2, RAP1A, FLRT3, CSPG2, COL4A1, TK1, DHFR, CDH3, HELLS, KIT, CXCL1, Ki67, MITF, p53, and p21.

17. A method of treatment for melanoma, the method comprising:
   (a) measuring the level of neurophilin-2 (NRP-2) mRNA in a sample obtained from a subject with melanoma by performing PCR;
   (b) measuring the level of melan-A (MART) mRNA in the sample obtained from the subject by performing PCR;

(c) calculating the value of NRP-2:MART from the levels obtained in steps (a) and (b);
(d) performing PCR using known quantities of NRP-2 and melan-A nucleic acids to generate a standard curve;
(e) calculating copy numbers of NRP-2 and melan-A in the sample using the standard curve generated in step (d) and the value calculated in step (c);
(f) (i) surgically removing the melanoma and administering adjuvant therapy and follow-up monitoring if the copy number of NRP-2:MART is increased relative to a reference level; and
  (ii) surgically removing the melanoma and not administering adjuvant therapy if the copy number of NRP-2:MART is not increased relative to a reference level.

* * * * *